US012599658B2

(12) United States Patent
Früh et al.

(10) Patent No.: US 12,599,658 B2
(45) Date of Patent: Apr. 14, 2026

(54) HEPATITIS B VIRUS-SPECIFIC T CELL RESPONSES

(71) Applicant: Oregon Health & Science University, Portland, OR (US)

(72) Inventors: Klaus J. Früh, Portland, OR (US); Louis J. Picker, Portland, OR (US); Benjamin J. Burwitz, Portland, OR (US); Scott G. Hansen, Portland, OR (US); Jonah B. Sacha, Beaverton, OR (US)

(73) Assignee: Oregon Health & Science University, Portland, OR (US)

( * ) Notice: Subject to any disclaimer, the term of this patent is extended or adjusted under 35 U.S.C. 154(b) by 1068 days.

(21) Appl. No.: 17/616,939

(22) PCT Filed: Jun. 5, 2020

(86) PCT No.: PCT/US2020/036480
§ 371 (c)(1),
(2) Date: Dec. 6, 2021

(87) PCT Pub. No.: WO2020/247858
PCT Pub. Date: Dec. 10, 2020

(65) Prior Publication Data
US 2022/0257748 A1 Aug. 18, 2022

Related U.S. Application Data

(60) Provisional application No. 62/858,764, filed on Jun. 7, 2019.

(51) Int. Cl.
| | |
|---|---|
| *A61K 39/12* | (2006.01) |
| *A61K 39/00* | (2006.01) |
| *A61K 40/11* | (2025.01) |
| *A61K 40/46* | (2025.01) |
| *A61K 47/30* | (2006.01) |
| *A61P 31/12* | (2006.01) |

(52) U.S. Cl.
CPC ...... *A61K 39/12* (2013.01); *A61K 39/001129* (2018.08); *A61K 40/11* (2025.01); *A61K 40/46* (2025.01); *A61K 47/30* (2013.01); *A61P 31/12* (2018.01); *A61K 2039/5256* (2013.01); *A61K 2039/572* (2013.01)

(58) Field of Classification Search
None
See application file for complete search history.

(56) References Cited

U.S. PATENT DOCUMENTS

| | | |
|---|---|---|
| 5,168,062 A | 12/1992 | Stinski et al. |
| 5,385,839 A | 1/1995 | Stinski |
| 2006/0020110 A1 | 1/2006 | Sallberg |
| 2007/0055049 A1 | 3/2007 | Grey et al. |
| 2010/0142523 A1 | 6/2010 | Ohman et al. |
| 2013/0136765 A1 | 5/2013 | Usami et al. |
| 2014/0141035 A1 | 5/2014 | Sun et al. |
| 2018/0133321 A1 | 5/2018 | Picker et al. |

FOREIGN PATENT DOCUMENTS

| | | |
|---|---|---|
| WO | WO-0116163 A2 | 3/2001 |
| WO | WO-2014135209 A1 | 9/2014 |
| WO | WO-2020247858 A1 | 12/2020 |

OTHER PUBLICATIONS

Heathcote et al., Hepatology, Aug. 1999, 30(2):531-536 (Year: 1999).*
Akbar et al., Vaccines (Basel), Sep. 30, 2022, 10(10):1644, 11 pages (Year: 2022).*
Suarez and Zoulim, eGastroenterology, 2023, 1:3100021, 9 pages (Year: 2023).*
Janeway et al., "The Generation of T-cell Receptor Ligands," Immunobiology: The Immune System in Health and Disease 5th Edition, Garland Science, New York, United States (2001).
De Rosa, S., "Vaccine applications of flow cytometry", Methods 57(3): 383-391, Elsevier, Amsterdam, Netherlands (Jan. 2012).
Bolton, D. et al., "Flow cytometry and the future of vaccine development," Expert Review of Vaccines: 779-789, Taylor & Francis Online, (Jan. 2014).
Maecker, H., "Multiparameter Flow Cytometry Monitoring of T Cell Responses", HIV Protocols: 375-391, Springer Nature Link, (Jan. 2009).
Zhang, Y., et al., "Hepatitis B virus core antigen epitopes presented by HLA-A2 single-chain trimers induce functional epitope-specific CD8+T-cell responses in HLA-A2[1]1/Kb transgenic mice," Immunology 121(1):105-112, Wiley-Blackwell Publishing Ltd., United Kingdom (May 2007).
Burwitz, B., et al., "MHC-E-Restricted CDS+ T Cells Target Hepatitis B Virus-Infected Human Hepatocytes", J Immunol, 204(8):2169-2176, American Association of Immunologists, United States (Apr. 2020).
Joint Committee on Vaccination and Immunisation. "Chapter 18 Hepatitis B". Immunisation Against Infectious Disease ("The Green Book") (3rd edition (Chapter 18) p. 468). Stationery Office, United Kingdom (2006).
Verweij, M., et al., "Targeting HLA-E for prostate cancer immunotherapy," J Immunol 200(1_Supplement):179.8-179.8, Oregon Health and Science University, United States (May 2018).
Braud, V., et al., "HLA-E binds to natural killer cell receptors CD94/NKG2A, B and C," Nature 391(6669):795-799, Nature Publishing Group, United Kingdom (Feb. 1998).
Kochan, G., et al., "Role of non-classical MHC class I molecules in cancer immunosuppression," Oncoimmunology 2(11):e26491, Landes Bioscience, United States (Nov. 2013).

(Continued)

*Primary Examiner* — Stacy B Chen
(74) *Attorney, Agent, or Firm* — Fox Rothschild LLP

(57) ABSTRACT

The present disclosure relates to methods to generate an immune response for the treatment or prevention of hepatitis B virus infection. This disclosure also relates to methods to generate MHC-E and/or MHC-II restricted CD8+ T cells for the treatment or prevention of hepatitis B virus infection.

6 Claims, 8 Drawing Sheets

Figure 1A:
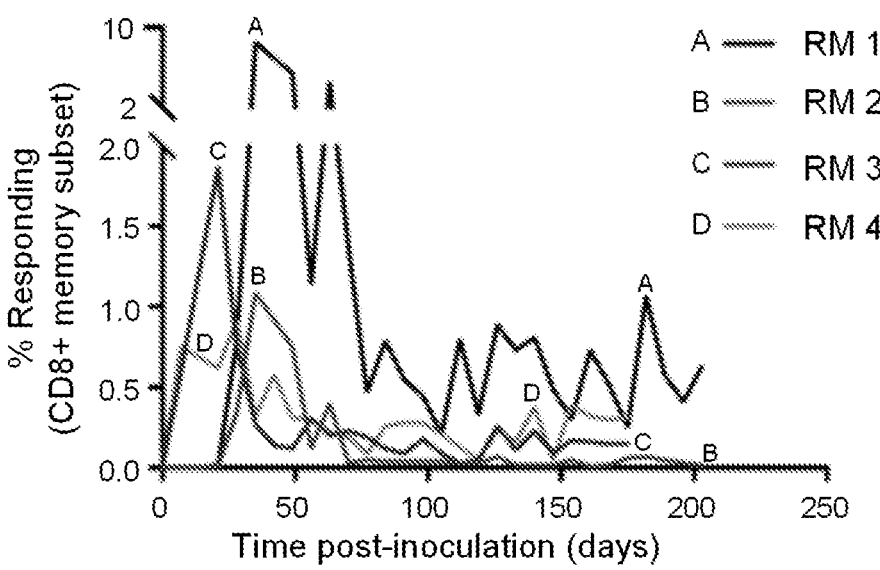

Specification includes a Sequence Listing.

(56)          References Cited

OTHER PUBLICATIONS

Wilkinson, G., et al., "Modulation of natural killer cells by human cytomegalovirus," J Clin Virol 41(3):206-212, Elsevier, Netherlands (Mar. 2008).

Fruh, K., and Picker, L., "CD8+ T cell programming by cytomegalovirus vectors: applications in prophylactic and therapeutic vaccination," Curr Opin Immunol 47:52-56, Elsevier, Netherlands (Aug. 2017).

Hansen, S., et al., "Prevention of tuberculosis in rhesus macaques by a cytomegalovirus-based vaccine," Nat Med 24(2):130-143, Nature Publishing Group, United Kingdom (Jan. 2018).

Hansen, S., et al., "Immune clearance of highly pathogenic SIV infection," Nature 502(7469):100-104, Nature Publishing Group, United Kingdom (Oct. 2013).

Braud, V., et al., "The human major histocompatibility complex class Ib molecule HLA-E binds signal sequence-derived peptides with primary anchor residues at positions 2 and 9," Eur J Immunol 27(5):1164-1169, Wiley-VCH Verlag, Germany (May 1997).

Hansen, S., et al., "Effector memory T cell responses are associated with protection of rhesus monkeys from mucosal simian immunodeficiency virus challenge," Nat Med 15(3):292-299, Nature Publishing Group, United Kingdom (Mar. 2009).

Hansen, S., et al., "Cytomegalovirus vectors expressing Plasmodium knowlesi antigens induce immune responses that delay parasitemia upon sporozoite challenge," PLoS One 14(1):e0210252, Public Library of Science, United States (Jan. 2019).

Altschul, S.F. and Gish W., "Local Alignment Statistics," Methods in Enzymology 266:460-480, Academic Press, United States (1996).

Altschul, S.F., et al., "Basic Local Alignment Search Tool," Journal of Molecular Biology 215(3):403-410, Elsevier, Netherlands (Oct. 1990).

Andre, S., et al., "Increased Immune Response Elicited by DNA Vaccination With a Synthetic gp120 Sequence With Optimized Codon Usage," Journal of Virology 72(2):1497-1503, American Society For Microbiology, United States (Feb. 1998).

Bertoletti, A. and Ferrari, C., "Adaptive Immunity in HBV Infection," Journal of Hepatology 64(1 Suppl):S71-S83, Elsevier, Netherlands (Apr. 2016).

Bhattacharya, D. and Thio, C.L., "Review of Hepatitis B Therapeutics," Clinical Infectious Diseases: an Official Publication of the Infectious Diseases Society of America 51(10):1201-1208, Oxford University Press, United States (Nov. 2010).

Chang, W.L and Barry, P.A, "Cloning of the Full-length Rhesus Cytomegalovirus Genome as an Infectious and Self-Excisable Bacterial Artificial Chromosome for Analysis of Viral Pathogenesis," Journal of Virology 77(9):5073-5083, American Society For Microbiology, United States (May 2003).

Corpet, F., "Multiple Sequence Alignment With Hierarchical Clustering," Nucleic Acids Research 16(22):10881-10890, Oxford University Press, England (Nov. 1988).

Felgner, J.H., et al., "Enhanced Gene Delivery and Mechanism Studies With a Novel Series of Cationic Lipid Formulations," Journal of Biological Chemistry 269(4):2550-2561, American Society for Biochemistry and Molecular Biology, United States (Jan. 1994).

Fisicaro, P., et al., "Early Kinetics of Innate and Adaptive Immune Responses During Hepatitis B Virus Infection," Gut 58(7):974-982, British Medical Assn, England (Jul. 2009).

Gill, U.S. and Kennedy, P.T.F., "Current Therapeutic Approaches for HBV Infected Patients," Journal of Hepatology 67(2):412-414, Elsevier, Netherlands (Aug. 2017).

Gish, W. and States, D.J., "Identification of Protein Coding Regions by Database Similarity Search," Nature Genetics 3(3):266-272, Nature Publishing Group, United States (Mar. 1993).

Goodman-Snitkoff, G., et al., "Role of Intrastructural/intermolecular Help in Immunization With Peptide-phospholipid Complexes," Journal of Immunology 147(2):410-415, American Association of Immunologists, United States (Jul. 1991).

Hancock, J.M and Armstrong, J.S., "SIMPLE34: an Improved and Enhanced Implementation for Vax and Sun Computers of the Simple Algorithm for Analysis of Clustered Repetitive Motifs in Nucleotide Sequences,"Computer Applications in the Biosciences 10(1):67-70, Oxford University Press, England (Feb. 1994).

Hansen, S.G., et al., "Broadly Targeted Cd8+ T Cell Responses Restricted by Major Histocompatibility Complex E," Science 351(6274):714-720, American Association for the Advancement of Science, United States (Feb. 2016).

Hansen, S.G., et al., "Cytomegalovirus Vectors Violate CD8+ T Cell Epitope Recognition Paradigms," Science 340(6135):1237874, American Association for the Advancement of Science, United States (May 2013).

Higgins, D.G. and Sharp, P.M., "CLUSTAL: A Package for Performing Multiple Sequence Alignment on a Microcomputer," Gene 73(1):237-244, Elsevier/North-Holland, Netherlands (Dec. 1988).

Higgins, D.G. and Sharp, P.M., "Fast and Sensitive Multiple Sequence Alignments on a Microcomputer," Computer Applications in the Biosciences 5(2):151-153, Oxford University Press, England (Apr. 1989).

Huang, X., et al., "Parallelization of a Local Similarity Algorithm," Computer Applications in the Biosciences 8(2):155-165, Oxford University Press, England (Apr. 1992).

International Search Report and Written Opinion for Application No. PCT/US2020/036480, mailed on Nov. 4, 2020, 13 pages.

Joosten, S.A., et al., "Characteristics of HLA-E Restricted T-Cell Responses and Their Role in Infectious Diseases," Journal of Immunology Research 2016:2695396, Hindawi Publishing Corporation, Egypt (Sep. 2016).

Kakimi, K., et al., "Immunogenicity and Tolerogenicity of Hepatitis B Virus Structural and Nonstructural Proteins: Implications for Immunotherapy of Persistent Viral Infections," Journal of Virology 76(17): 8609-8620, American Society For Microbiology, United States (Sep. 2002).

Karlin, S. and Altschul, S.E., "Methods for Assessing the Statistical Significance of Molecular Sequence Features by using General Scoring Schemes," Proceedings of the National Academy of Sciences USA 87(6):2264-2268, National Academy of Sciences, United States (Mar. 1990).

Karlin, S. and Altschul, S.F., "Applications and Statistics for Multiple High-scoring Segments in Molecular Sequences," Proceedings of the National Academy of Sciences USA 90(12):5873-5877, National Academy of Sciences, United States (Jun. 1993).

Kong, X., et al., "γδT Cells Drive Myeloid-derived Suppressor Cell-mediated CD8+ T Cell Exhaustion in Hepatitis B Virus-induced Immunotolerance," Journal of Immunology 193(4):1645-1653, American Association of Immunologists, United States (Aug. 2014).

Kurktschiev, P.D., et al., "Dysfunctional CD8+ T Cells in Hepatitis B and C are Characterized by a Lack of Antigen-specific T-bet Induction," The Journal of Experimental Medicine 211(10):2047-2059, Rockefeller University Press, United States (Sep. 2014).

Maini, M.K., et al., "Direct ex Vivo Analysis of Hepatitis B Virus-specific CD8(+) T Cells Associated With The Control of Infection," Gastroenterology 117(6):1386-1396, W.B. Saunders, United States (Dec. 1999).

Marshall, E.E., et al., "Enhancing Safety of Cytomegalovirus-based Vaccine Vectors by Engaging Host Intrinsic Immunity," Science Translational Medicine 11(501):eaaw2603, American Association for the Advancement of Science, United States (Jul. 2019).

Michel, M.L., et al., "DNA-mediated Immunization to The Hepatitis B Surface Antigen in Mice: Aspects of the Humoral Response Mimic Hepatitis B Viral Infection in Humans," Proceedings of the National Academy of Sciences of the United States of America 92(12):5307-5311, National Academy of Sciences, United States (Jun. 1995).

Milich, D.R., "The Concept of Immune Tolerance in Chronic Hepatitis B Virus Infection Is Alive and Well," Gastroenterology 151(5):801-804, W.B. Saunders, United States (Nov. 2016).

Miller, M.D., et al., "Vaccination of Rhesus Monkeys With Synthetic Peptide in a Fusogenic Proteoliposome Elicits Simian Immunodeficiency Virus-specific Cd8+ Cytotoxic T Lymphocytes," Journal of Experimental Medicine 176(6):1739-1744, Rockefeller University Press, United States (Dec. 1992).

(56)                    References Cited

OTHER PUBLICATIONS

Myers, E.W. and Miller, W., "Optimal Alignments in Linear Space," Computer Applications in the Biosciences 4(1):11-17, Oxford University Press, England (Mar. 1988).

Needleman, S.B. and Wunsch, C.D., "A General Method Applicable to the Search for Similarities in the Amino Acid Sequence of Two Proteins," Journal of Molecular Biology 48(3):443-453, Elsevier, Netherlands (Mar. 1970).

Pearson, W.R. and Lipman, D.J., "Improved Tools for Biological Sequence Comparison," Proceedings of the National Academy of Sciences of the United States of America 85(8):2444-2448, National Academy of Sciences, United States (Apr. 1988).

Pearson, W.R., "Using the FASTA Program to Search Protein and DNA Sequence Databases," Methods in Molecular Biology 24:307-331, Humana Press, United States (Feb. 1994).

Phillips, S., et al., "CD8(+) T Cell Control of Hepatitis B Virus Replication: Direct Comparison Between Cytolytic and Noncytolytic Functions," Journal of Immunology 184(1):287-295, American Association of Immunologists, United States (Jan. 2010).

Rehermann, B. and Bertoletti, A., "Immunological Aspects of Antiviral Therapy of Chronic Hepatitis B Virus and Hepatitis C Virus Infections," Hepatology 61(2):712-721, Wiley, United States (Feb. 2015).

Salisbury, D., et al., (eds.), "Hepatitis B," Ch. 18, Part 2—The disease, vaccinations and vaccines, in Immunisation against infectious disease, Third edition, pp. 161-184, The Stationary Office, Great Britain (2006).

Senaldi, G., et al., "Class I and Class II Major Histocompatibility Complex Antigens on Hepatocytes: Importance of the Method of Detection and Expression in Histologically Normal and Diseased Livers," Journal of Clinical Pathology 44(2):107-114, BMJ Pub. Group, England (Feb. 1991).

Smith, T.F. and Waterman, M.S., "Comparison of Biosequences," Advances in Applied Mathematics 2(4):482-489, Academic Press, Inc., United States (Dec. 1981).

Ulmer, J.B., et al., "Heterologous Protection against Influenza by injection of DNA Encoding a Viral Protein," Science 259(5102):1745-1749, American Association for the Advancement of Science, United States (Mar. 1993).

Warming, S., et al., "Simple and Highly Efficient BAC Recombineering Using galk Selection," Nucleic Acids Research 33(4):e36, Oxford University Press, England (Feb. 2005).

Wu, H.L., et al., "The Role of MHC-E in T Cell Immunity Is Conserved among Humans, Rhesus Macaques, and Cynomolgus Macaques," Journal of Immunology 200(1):49-60, American Association of Immunologists, United States (Jan. 2018).

Zhang, Y., et al., "HBsAg Seroclearance or Seroconversion Induced by Peg-interferon Alpha and Lamivudine or Adefovir Combination Therapy in Chronic Hepatitis B Treatment: a Meta-analysis and Systematic Review," Spanish Journal of Digestive Diseases 108(5):263-270, Aran Ediciones, Spain (May 2016).

Zong, L., et al., "Breakdown of Adaptive Immunotolerance induces hepatocellular carcinoma in HBsAg-tg mice," Nature Communications 10(1):221, Nature Pub. Group, England (Jan. 2019).

* cited by examiner

Consecutive HBV-core 15mers

| ■ MHC-Ia restricted | □ MHC-II restricted |
| ▨ MHC-E restricted | ▧ Indeterminate |

A

Core 7

B

Core 14

Amino Acid Position

SEQUENCE LISTING

```
<160> NUMBER OF SEQ ID NOS: 18

<210> SEQ ID NO 1
<211> LENGTH: 35
<212> TYPE: DNA
<213> ORGANISM: Artificial Sequence
<220> FEATURE:
<223> OTHER INFORMATION: left reverse primer

<400> SEQUENCE: 1
catcgagcta gcaccatgga gaacatcaca tcagg                              35

<210> SEQ ID NO 2
<211> LENGTH: 35
<212> TYPE: DNA
<213> ORGANISM: Artificial Sequence
<220> FEATURE:
<223> OTHER INFORMATION: right forward primer

<400> SEQUENCE: 2
gtgttgatag gataggggaa tgtataccca aagac                              35

<210> SEQ ID NO 3
<211> LENGTH: 35
<212> TYPE: DNA
<213> ORGANISM: Artificial Sequence
<220> FEATURE:
<223> OTHER INFORMATION: right reverse primer

<400> SEQUENCE: 3
gtctttgggt atacattccc ctatcctatc aacac                              35

<210> SEQ ID NO 4
<211> LENGTH: 67
<212> TYPE: DNA
<213> ORGANISM: Artificial Sequence
<220> FEATURE:
<223> OTHER INFORMATION: left forward primer

<400> SEQUENCE: 4
ggaatcgtcg actcaagcgt aatctggaac atcgtatggg taaagattga cgataaggga     60
gaggcag                                                             67

<210> SEQ ID NO 5
<211> LENGTH: 42
<212> TYPE: DNA
<213> ORGANISM: Artificial Sequence
<220> FEATURE:
<223> OTHER INFORMATION: forward primer

<400> SEQUENCE: 5
gtggtaccct cgaggattgg ggaccctgcg ctgaacatgg ag                       42

<210> SEQ ID NO 6
```

-continued

```
<211> LENGTH: 40
<212> TYPE: DNA
<213> ORGANISM: Artificial Sequence
<220> FEATURE:
<223> OTHER INFORMATION: reverse primer

<400> SEQUENCE: 6
tcagtcgacc taagcgtaat ctggaacatc gtatgggtac                          40

<210> SEQ ID NO 7
<211> LENGTH: 37
<212> TYPE: DNA
<213> ORGANISM: Artificial Sequence
<220> FEATURE:
<223> OTHER INFORMATION: forward primer

<400> SEQUENCE: 7
ctgctagcat ggacattgac ccttataaag aatttgg                             37

<210> SEQ ID NO 8
<211> LENGTH: 32
<212> TYPE: DNA
<213> ORGANISM: Artificial Sequence
<220> FEATURE:
<223> OTHER INFORMATION: reverse primer

<400> SEQUENCE: 8
ctaggtacca cattgagatt cccgagattg ag                                  32

<210> SEQ ID NO 9
<211> LENGTH: 75
<212> TYPE: DNA
<213> ORGANISM: Artificial Sequence
<220> FEATURE:
<223> OTHER INFORMATION: Rh110 S/PolN forward

<400> SEQUENCE: 9
gatcacgtca ttgacaccgg cctcccacca gctctcacat tctccgcatc accatggaga    60
acatcacatc aggat                                                     75

<210> SEQ ID NO 10
<211> LENGTH: 79
<212> TYPE: DNA
<213> ORGANISM: Artificial Sequence
<220> FEATURE:
<223> OTHER INFORMATION: Rh110 S/PolN reverse

<400> SEQUENCE: 10
caaaatatta ttacatggta cgcaatttat tgtctatttt cgttatttgt ttattcaagc    60
gtaatctgga acatcgtat                                                 79

<210> SEQ ID NO 11
<211> LENGTH: 78
<212> TYPE: DNA
<213> ORGANISM: Artificial Sequence
<220> FEATURE:
<223> OTHER INFORMATION: Rh110 Core/PolC forward

<400> SEQUENCE: 11
gatcacgtca ttgacaccgg cctcccacca gctctcacat tctccgcatc accatggaca    60 ttgacccctta taaagaat                                                 78

<210> SEQ ID NO 12
<211> LENGTH: 79
```

-continued

```
<212> TYPE: DNA
<213> ORGANISM: Artificial Sequence
<220> FEATURE:
<223> OTHER INFORMATION: Rh110 Core/PolC reverse

<400> SEQUENCE: 12
caaaatatta ttacatggta cgcaatttat tgtctatttt cgttatttgt ttatctaagc      60
gtaatctgga acatcgtat      79

<210> SEQ ID NO 13
<211> LENGTH: 55
<212> TYPE: DNA
<213> ORGANISM: Artificial Sequence
<220> FEATURE:
<223> OTHER INFORMATION: forward primer

<400> SEQUENCE: 13
ctgctagcat ggattacaag gatgacaagg acatcgaccc ttataaagaa tttgg      55

<210> SEQ ID NO 14
<211> LENGTH: 32
<212> TYPE: DNA
<213> ORGANISM: Artificial Sequence
<220> FEATURE:
<223> OTHER INFORMATION: reverse primer

<400> SEQUENCE: 14
ctagtcgaca cattgagatt cccgagattg ag      32

<210> SEQ ID NO 15
<211> LENGTH: 84
<212> TYPE: DNA
<213> ORGANISM: Artificial Sequence
<220> FEATURE:
<223> OTHER INFORMATION: forward primer

<400> SEQUENCE: 15
gggaaatcac gtcatcaggc tgggtagtca acatgggcat acgaaacttg cccgaataga      60
tgctctcact taacggctga catg      84

<210> SEQ ID NO 16
<211> LENGTH: 84
<212> TYPE: DNA
<213> ORGANISM: Artificial Sequence
<220> FEATURE:
<223> OTHER INFORMATION: reverse primer

<400> SEQUENCE: 16
ccagaatgtg ctctactttt tggccagcgg gttggatgat ttcgcgcgtc atggactgct      60
tcactgtagc ttagtacgtt aaac      84

<210> SEQ ID NO 17
<211> LENGTH: 15
<212> TYPE: PRT
<213> ORGANISM: Artificial Sequence
<220> FEATURE:
<223> OTHER INFORMATION: antigen

<400> SEQUENCE: 17

Pro Ser Val Arg Asp Leu Leu Asp Thr Ala Ser Ala Leu Tyr Arg
1               5                   10                  15

<210> SEQ ID NO 18
<211> LENGTH: 15
```

-continued

```
<212> TYPE: PRT
<213> ORGANISM: Artificial Sequence
<220> FEATURE:
<223> OTHER INFORMATION: antigen

<400> SEQUENCE: 18

Thr Ala Leu Arg Gln Ala Ile Leu Cys Trp Gly Glu Leu Met Thr
1               5                   10                  15
```

HEPATITIS B VIRUS-SPECIFIC T CELL RESPONSES

CROSS REFERENCE TO RELATED APPLICATIONS

This application is a 35 U.S.C. § 371 National Phase Application of International Application No. PCT/US2020/036480, filed Jun. 5, 2020, which claims the benefit of U.S. Provisional Application No. 62/858,764, filed Jun. 7, 2019, each of which is hereby incorporated by reference in its entirety.

STATEMENT REGARDING FEDERALLY-SPONSORED RESEARCH AND DEVELOPMENT

This invention was made with government support under grant numbers R01 AI117802, R01 AI129703, R01 AI140888, and P51OD011092 awarded by the National Institutes of Health. The government has certain rights in the invention.

REFERENCE TO SEQUENCE LISTING SUBMITTED ELECTRONICALLY

The content of the electronically submitted sequence listing in ASCII text file (Name: 4153_0110001_Seq-listing_ST25; Size: 4,336 bytes; and Date of Creation: Nov. 30, 2021) filed with the application is incorporated herein by reference in its entirety.

BACKGROUND OF THE INVENTION

Chronic hepatitis B virus infection (CHB) is a major global health concern, affecting 247 million individuals worldwide and causing 887,000 deaths annually. While there is an effective prophylactic vaccine available, 10-15% of individuals do not respond adequately to vaccination and are not protected against hepatitis B virus (HBV) infection (Joint Committee on Vaccination and Immunisation. Hepatitis B. In Immunisation Against Infectious Disease, 3rd ed. p. 468.). CHB can lead to progressive liver dysfunction, cirrhosis, and in some cases hepatocellular carcinoma. There are multiple treatment options for CHB, including pegy-lated-IFNα and reverse-transcriptase inhibitors (Bhattacha-rya, D., and C. L. Thio. 2010. Review of hepatitis B therapeutics. Clin. Infect. Dis. 51: 1201-1208.), but these treatments are rarely curative (Zhang et al. 2016. HBsAg seroclearance or seroconversion induced by peg-interferon alpha and lamivudine or adefovir combination therapy in chronic hepatitis B treatment: a meta-analysis and system-atic review. Rev Esp Enferm Dig 108: 263-270.).

Developing cellular immunotherapeutic strategies for CHB is supported by the fact that 90-95% of acutely HBV-infected adults mount broad, highly functional HBV-specific T cell responses and subsequently clear infection (Maini et al. 1999. Direct ex vivo analysis of hepatitis B virus-specific CD8(+) T cells associated with the control of infection. Gastroenterology 117: 1386-1396; Phillips et al. 2010. CD8(+) T cell control of hepatitis B virus replication: direct comparison between cytolytic and noncytolytic func-tions. J. Immunol. 184: 287-295; Fisicaro et al. 2009. Early kinetics of innate and adaptive immune responses during hepatitis B virus infection. Gut 58: 974-982.). In contrast, patients progressing to CHB exhibit narrowly-focused, low-frequency, functionally-exhausted HBV-specific T cell responses (Bertoletti, A., and C. Ferrari. 2016. Adaptive immunity in HBV infection. J. Hepatology 64: S71-S83; Rehermann, B., and A. Bertoletti. 2015. Immunological aspects of antiviral therapy of chronic hepatitis B virus and hepatitis C virus infections. Hepatology 61: 712-721; Kurktschiev et al. 2014. Dysfunctional CD8+ T cells in hepatitis B and C are characterized by a lack of antigen-specific T-bet induction. J. Exp. Med. 211: 2047-2059.). Therefore, many immunotherapeutic strategies currently in development focus on augmentation of HBV-specific T cell immunity.

Immunotherapies currently under investigation are designed to harness the immune system to better target HBV infected hepatocytes and include immune stimulation with pattern recognition receptor agonists, check point inhibitor blockades, therapeutic vaccines, and adoptive T cell therapy (Gill, U. S., and P. T. F. Kennedy. 2017. Current therapeutic approaches for HBV infected patients. J. Hepatology 67: 412-414.). A common hurdle facing HBV immunotherapies is T cell immunotolerance (Zong et al. 2019. Breakdown of adaptive immunotolerance induces hepatocellular carci-noma in HBsAg-tg mice. Nature Communications 10: 221; Kong et al. 2014. γδT cells drive myeloid-derived suppres-sor cell-mediated CD8+ T cell exhaustion in hepatitis B virus-induced immunotolerance. J. Immunol. 193: 1645-1653; Milich, D. R. 2016. The Concept of Immune Toler-ance in Chronic Hepatitis B Virus Infection Is Alive and Well. Gastroenterology 151: 801-804.). The initial triggers of immunotolerance, which distinguishes patients that suc-cessfully clear acute HBV viremia from those that do not, is not completely understood. However, it is likely in part a consequence of the immunotolerant environment of the liver. Thus, in order to successfully clear CHB via immu-notherapy, T cell immunotolerance must be overcome. Unfortunately, no immunotherapies to date have consis-tently achieved this goal, and this reality has been exacer-bated by the lack of physiologically relevant animal models of CHB.

T cell-based immunotherapies for CHB must provide lasting reversal of T cell exhaustion or sustained viral suppression. Given the difficulty in reversing the dysfunc-tion of established HBV-specific T cells in CHB patients, the most effective way to augment HBV-specific T cell immu-nity may be to engender or impart a completely unique set of T cell responses through therapeutic vaccination or adop-tive T cell therapy. Unfortunately, generating such de novo responses is limited by patient-specific HLA expression and the HBV peptides that these molecules present on the hepatocyte surface. In contrast, if universally expressed, unconventional MHC-Ib T cell restriction elements that do not contribute to the natural, acute HBV-specific immune response could present HBV antigen on the hepatocyte surface, they could be targeted to elicit a totally distinct set of T cell responses not typically found in HBV infection. Thus, there is an urgent global need to develop curative therapeutics for HBV.

BRIEF SUMMARY OF THE INVENTION

The present disclosure relates to a method of generating an immune response to a hepatitis B virus (HBV) in a subject, the method comprising administering to the subject a CMV vector expressing a HBV antigen in an amount effective to elicit a CD8+ T cell response to the HBV antigen, wherein the CMV vector does not express an active UL128, UL130, UL146 and UL147 protein or orthologs thereof. In one embodiment, the HBV antigen is PSVRDLL-DTASALYR (SEQ ID NO: 17) or TALRQAILCWGELMT (SEQ ID NO: 18).

The present disclosure also relates to a method of treating chronic HBV infection in a subject, the method comprising administering to the subject a CMV vector expressing a HBV antigen in an amount effective to elicit a CD8+ T cell response to the HBV antigen, wherein the CMV vector does not express an active UL128, UL130, UL146 and UL147 protein or orthologs thereof. In one embodiment, the HBV antigen is PSVRDLLDTASALYR (SEQ ID NO: 17) or TALRQAILCWGELMT (SEQ ID NO: 18).

The present disclosure also relates to a CMV vector expressing a HBV antigen for use in generating an immune response to a HBV in a subject, wherein the CMV vector does not express an active UL128, UL130, UL146, and UL147 protein or orthologs thereof. In one embodiment, the HBV antigen is PSVRDLLDTASALYR (SEQ ID NO: 17) or TALRQAILCWGELMT (SEQ ID NO: 18).

The present disclosure also relates to a CMV vector expressing a HBV antigen for use in the treatment of a chronic HBV infection in a subject, wherein the CMV vector does not express an active UL128, UL130, UL146, and UL147 protein or orthologs thereof. In one embodiment, the HBV antigen is PSVRDLLDTASALYR (SEQ ID NO: 17) or TALRQAILCWGELMT (SEQ ID NO: 18).

The present disclosure also relates to use of a CMV vector expressing a HBV antigen in the manufacture of a medicament for use in generating an immune response to a HBV in a subject, wherein the CMV vector does not express an active UL128, UL130, UL146, and UL147 protein or orthologs thereof. In one embodiment, the HBV antigen is PSVRDLLDTASALYR (SEQ ID NO: 17) or TALRQAILCWGELMT (SEQ ID NO: 18).

The present disclosure also relates to use of a CMV vector expressing a HBV antigen in the manufacture of a medicament for the treatment of a chronic HBV infection, wherein the CMV vector does not express an active UL128, UL130, UL146, and UL147 protein or orthologs thereof. In one embodiment, the HBV antigen is PSVRDLLDTASALYR (SEQ ID NO: 17) or TALRQAILCWGELMT (SEQ ID NO: 18).

In one embodiment, the hepatitis B virus antigens are hepatitis B virus core, envelope, surface, X, or polymerase antigens. In some embodiments, the hepatitis B virus antigen has at least 50%, at least 60%, at least 70%, at least 75%, at least 80%, at least 85%, at least 90%, at least 95%, or 100% identity to PSVRDLLDTASALYR (SEQ ID NO: 17). In some embodiments, the hepatitis B virus antigen has at least 50%, at least 60%, at least 70%, at least 75%, at least 80%, at least 85%, at least 90%, at least 95%, or 100% identity to TALRQAILCWGELMT (SEQ ID NO: 18).

In another embodiment, at least 10% of the CD8+ T cells elicited by the CMV vector are restricted by MHC-E or an ortholog thereof, or MHC-II or an ortholog thereof. In another embodiment, at least 20%, at least 30%, at least 40%, at least 50%, at least 60% or at least 75% of the CD8+ T cells elicited by the CMV vector are restricted by MHC-E or an ortholog thereof, or MHC-II or an ortholog thereof. In another embodiment, fewer than 10% of the CD8+ T cells elicited by the CMV vector are restricted by MHC-class 1a or an ortholog thereof. In another embodiment, some of the CD8+ T cells restricted by MHC-E recognize peptides shared by at least 90% of other subjects immunized with the vector. In some embodiments, the CD8+ T cells restricted by MHC-E recognize a MHC-E supertope. In some embodiments, the MHC-E supertope has at least 50%, at least 60%, at least 70%, at least 75%, at least 80%, at least 85%, at least 90%, at least 95%, or 100% identity to PSVRDLLD-TASALYR (SEQ ID NO: 17). In some embodiments, the MHC-E supertope has at least 50%, at least 60%, at least 70%, at least 75%, at least 80%, at least 85%, at least 90%, at least 95%, or 100% identity to TALRQAILCWGELMT (SEQ ID NO: 18).

The present disclosure also relates to a method of generating CD8+ T cells that recognize MHC-E-HBV antigen peptide complexes, the method comprising: (a) administering to a first subject a recombinant CMV vector comprising a nucleic acid that expresses a HBV antigen, in an amount effective to generate a set of CD8+ T cells that recognize MHC-E/peptide complexes, wherein the CMV vector does not express an active UL128, UL130, UL146 and UL147 protein or orthologs thereof, (b) identifying a first CD8+ TCR from the set of CD8+ T cells, wherein the first CD8+ TCR recognizes a MHC-E/HBV antigen-derived peptide complex; (c) isolating one or more CD8+ T cells from a second subject; and (d) transfecting the one or more CD8+ T cells with an expression vector, wherein the expression vector comprises a nucleic acid sequence encoding a second CD8+ TCR and a promoter operably linked to the nucleic acid sequence encoding the second CD8+ TCR, wherein the second CD8+ TCR comprises CDR3α and CDR3β of the first CD8+ TCR, thereby generating CD8+ T cells that recognize a MHC-E/HBV antigen peptide complex.

The present disclosure also relates to a method of generating CD8+ T cells that recognize MHC-E-HBV antigen peptide complexes, the method comprising: (a) isolating from a first subject a first set of CD8+ T cells, wherein the first subject has been administered a recombinant CMV vector comprising a nucleic acid that expresses a HBV antigen, in an amount effective to generate a set of CD8+ T cells that recognize MHC-E/peptide complexes, wherein the CMV vector does not express an active UL128, UL130, UL146, and UL147 protein or orthologs thereof, (b) identifying a first CD8+ TCR from the first set of CD8+ T cells, wherein the first CD8+ TCR recognizes a MHC-E/HBV antigen-derived peptide complex; (c) isolating a second set of CD8+ T cells from a second subject; and (d) transfecting the second set of CD8+ T cells with an expression vector, wherein the expression vector comprises a nucleic acid sequence encoding a second CD8+ TCR and a promoter operably linked to the nucleic acid sequence encoding the second CD8+ TCR, wherein the second CD8+ TCR comprises CDR3α and CDR3β of the first CD8+ TCR, thereby generating CD8+ T cells that recognize a MHC-E/HBV antigen peptide complex.

In one embodiment, the recombinant CMV vector is a recombinant human CMV vector or a recombinant rhesus macaque CMV vector. In another embodiment, the hepatitis B virus antigens are hepatitis B virus core, envelope, surface, or polymerase antigens. In some embodiments, the hepatitis B virus antigen has at least 50%, at least 60%, at least 70%, at least 75%, at least 80%, at least 85%, at least 90%, at least 95%, or 100% identity to PSVRDLLD-TASALYR (SEQ ID NO: 17). In some embodiments, the hepatitis B virus antigen has at least 50%, at least 60%, at least 70%, at least 75%, at least 80%, at least 85%, at least 90%, at least 95%, or 100% identity to TALRQAILCWGELMT (SEQ ID NO: 18).

In one embodiment, the first CD8+ T cell recognizes specific MHC-E supertopes. In another embodiment, the second CD8+ T cell recognizes specific MHC-E supertopes. In some embodiments, the MHC-E supertope is PSVRDLL-DTASALYR (SEQ ID NO: 17) or TALRQAILCWGELMT (SEQ ID NO: 18). In some embodiments, the MHC-E supertope is PSVRDLLDTASALYR (SEQ ID NO: 17). In some embodiments, the MHC-E supertope is TALRQAILCWGELMT (SEQ ID NO: 18).

In another embodiment, the first CD8+ TCR is identified by DNA or RNA sequencing. In another embodiment, the nucleic acid sequence encoding the second CD8+ TCR is identical to the nucleic acid sequence encoding the first CD8+ TCR.

In one embodiment, the first subject is a human or nonhuman primate. In another embodiment, the subject is a nonhuman primate and the second subject is a human, and wherein the second CD8+ TCR is a chimeric nonhuman primate-human CD8+ TCR comprising the non-human primate CDR3α and CDR3β of the first CD8+ TCR. In another embodiment, the second CD8+ TCR comprises the non-human primate CDR1α, CDR2α, CDR3α, CDR1β, CDR2β, and CDR3β of the first CD8+ TCR. In another embodiment, the second CD8+ TCR comprises CDR1α, CDR2α, CDR3α, CDR1β, CDR2β, and CDR3β of the first CD8+ TCR. In another embodiment, the nucleic acid sequence encoding the second CD8+ TCR is identical to the nucleic acid sequence encoding the first CD8+ TCR. In another embodiment, the second CD8+ TCR is a chimeric CD8+ TCR. In another embodiment, the second CD8+ TCR comprises CDR1α, CDR2α, CDR3α, CDR13, CDR2β, and CDR3β of the first CD8+ TCR.

In one embodiment, administering the CMV vector to the first subject comprises intravenous, intramuscular, intraperitoneal, or oral administration of the CMV vector to the first subject. In another embodiment, the transfected CD8+ T cells are further administered to the second subject to treat or prevent HBV infection.

The present disclosure also relates to a CD8+ T cell generated by the methods described herein.

The present disclosure also relates to a method of treating or preventing a hepatitis B infection in a subject, the method comprising administering a CD8+ T cell described herein to the subject in need thereof. The present disclosure also relates to a CD8+ T cell for use in a method of treating or preventing a hepatitis B infection in a subject in need thereof. The present disclosure also relates to the use of a CD8+ T cell in the manufacture of a medicament in a method of treating or preventing a hepatitis B infection in a subject in need thereof.

BRIEF DESCRIPTION OF THE
DRAWINGS/FIGURES

Figure 1B:
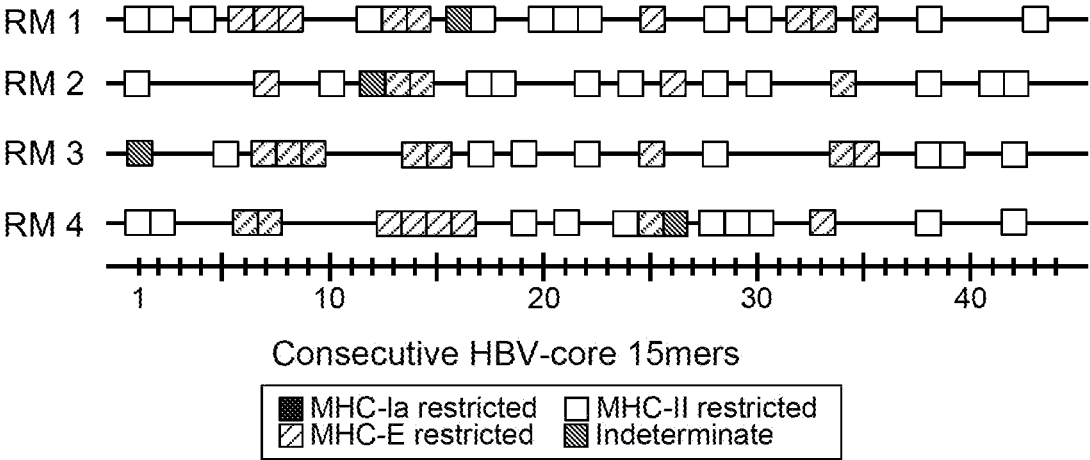
Figure 1C:
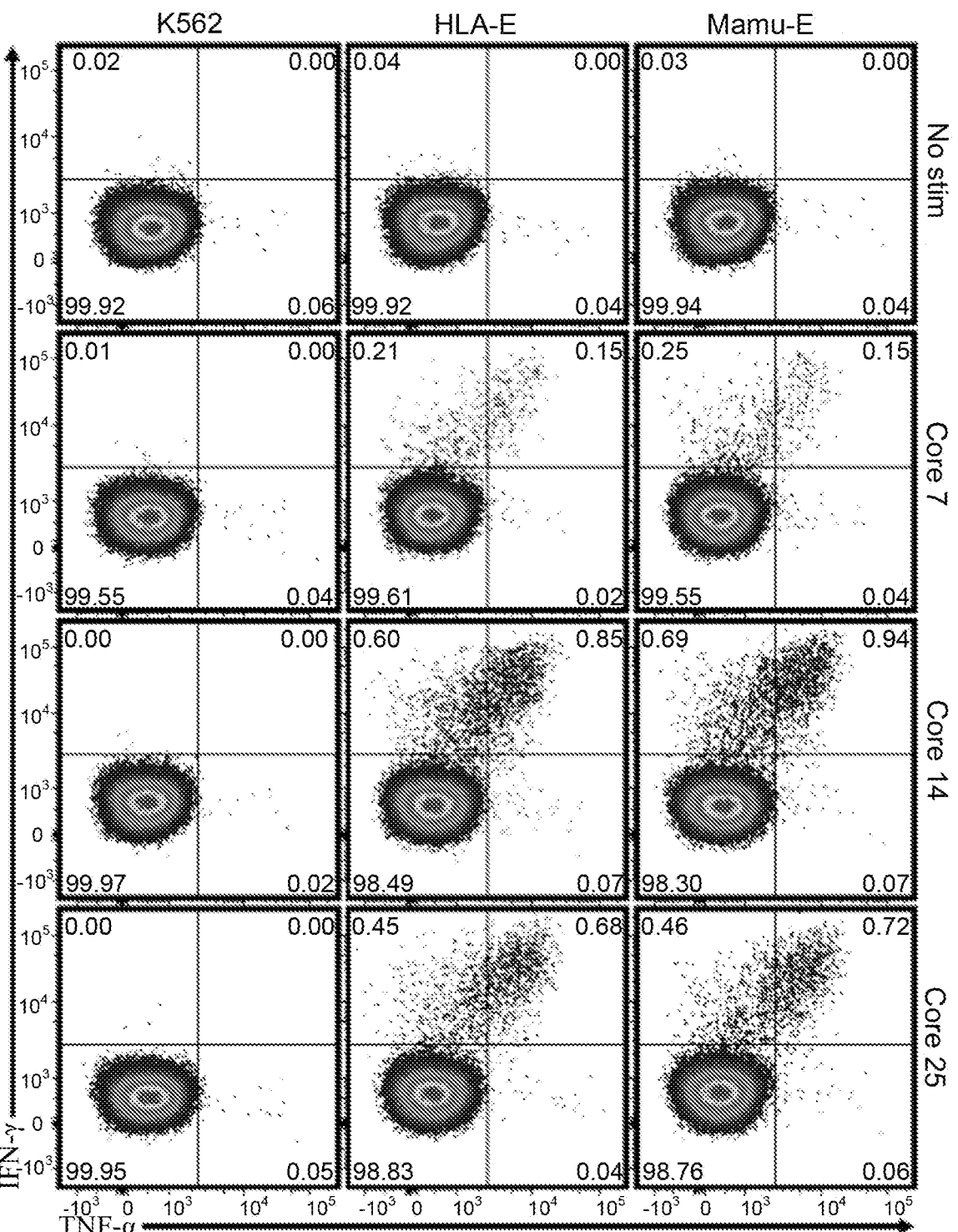

FIG. 1A shows the frequency of HBV-antigen specific CD8+ T cell responses of four Rhesus macaques (RM) inoculated with strain 68-1 RhCMV expressing HBV core, surface, and polymerase antigens (RhCMV/HBV 68-1). FIG. 1B shows CD8+ T cell response against individual peptides of HBV core antigens (HBcAg) Each HBcAg 15-mer is indicated by a box, color coded as shown to indicate MHC restriction. FIG. 1C shows response of CD8+ T cells isolated from inoculated RM to K562 cells transfected with either HLA-E or Mamu-E upon addition of HBcAg peptides.

Figure 2A:
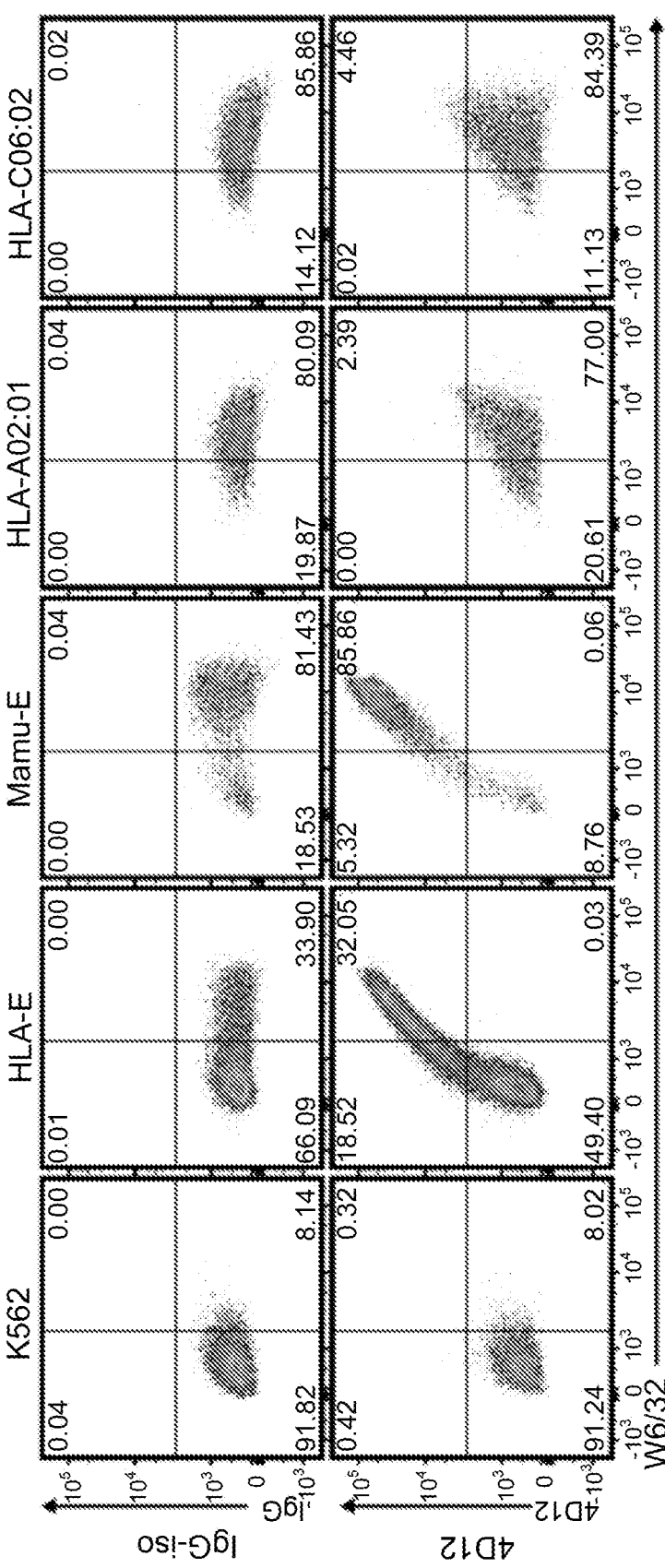
Figure 2B:
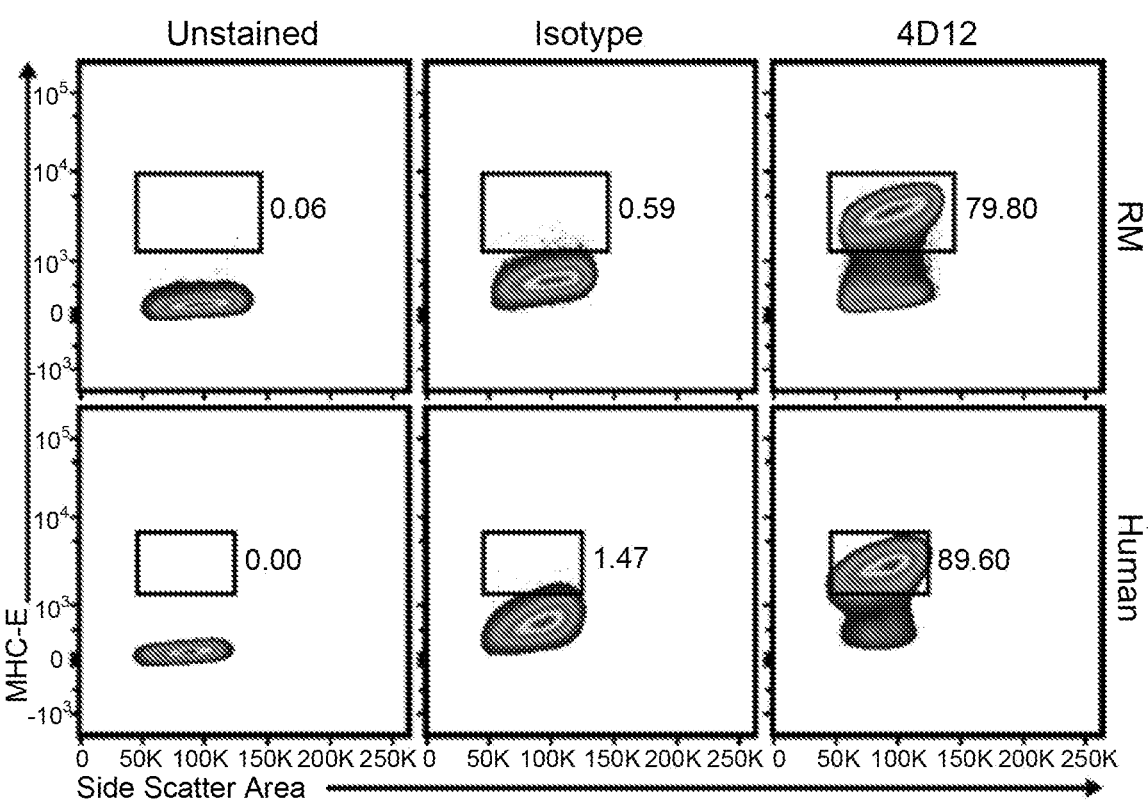
Figure 2C:
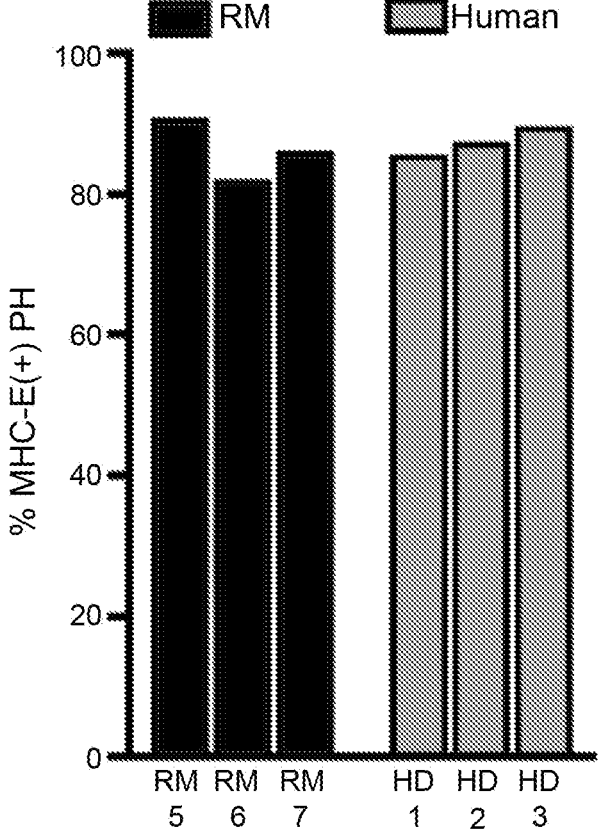
Figures 2D, 2E:
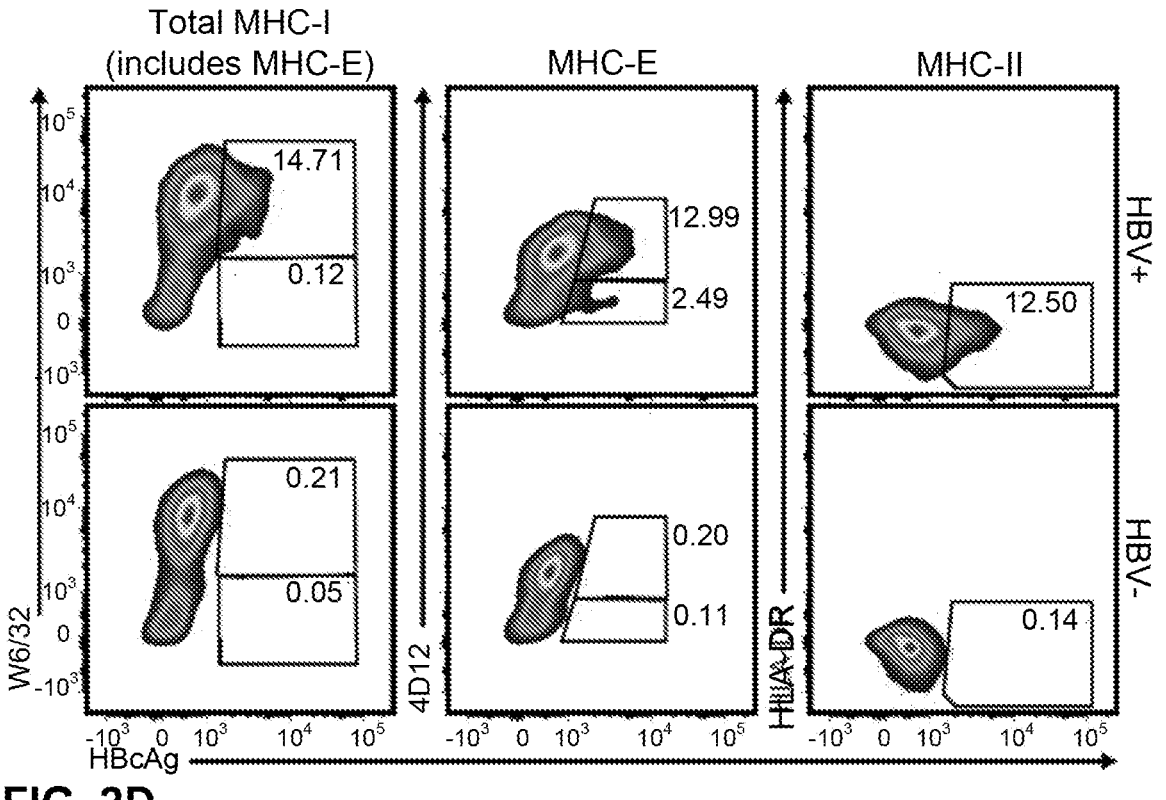

FIG. 2A shows staining with MHC-E specific antibody 4D12 of MHC-transfected cell lines. 4D12 staining was compared to match IgG-isotype control. In addition, cells were stained with the pan-MHC-I-specific antibody W6/32. FIG. 2B shows 4D12 staining of human and RM primary hepatocytes one day after liver perfusion and plating. Mouse IgG1 isotype was used to control for non-specific antibody binding by primary hepatocytes. FIG. 2C shows the quantification of the percent of MHC-E+ primary hepatocytes from FIG. 2B. FIG. 2D shows co-staining of surface MHC-I, MHC-E, or MHC-II and intracellular HBcAg of human donor primary hepatocytes at four days post-infection with HBV. FIG. 2E shows quantification of the percent of HBV+ primary hepatocytes from FIG. 2D.

Figure 3A:
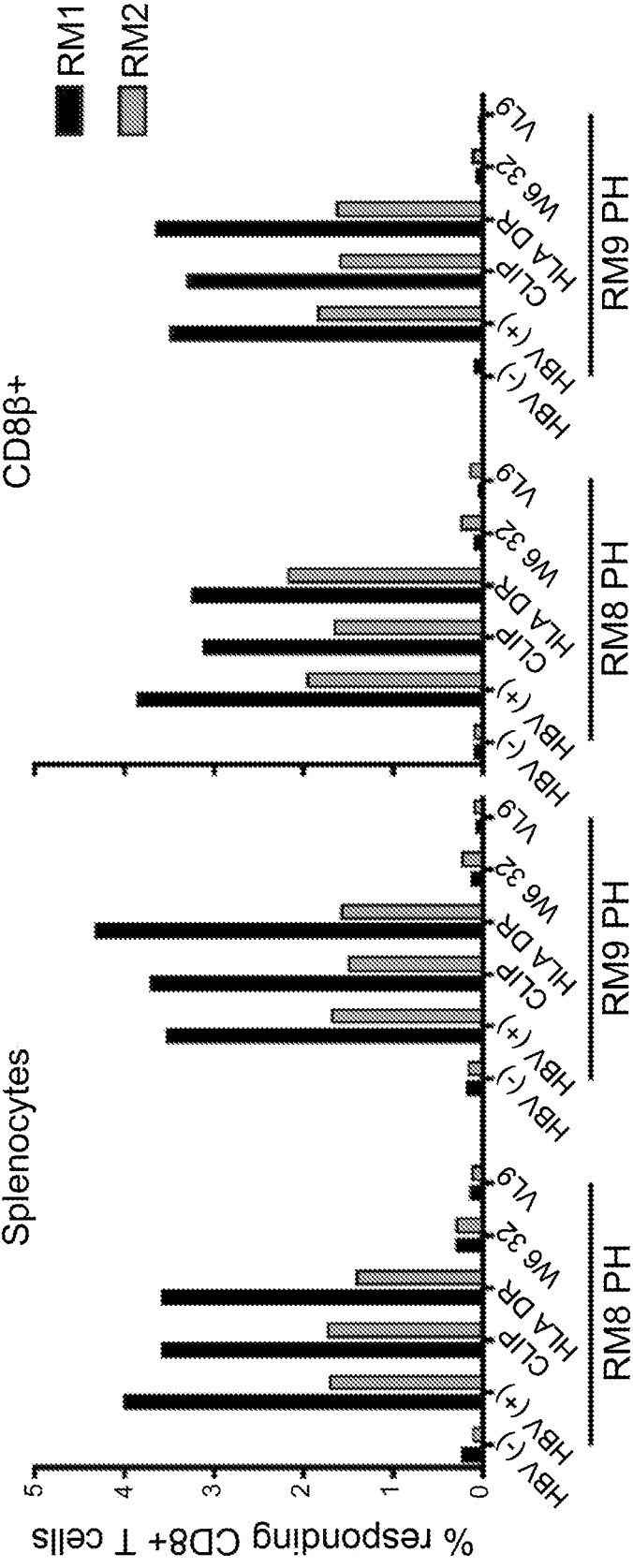
Figure 3B:
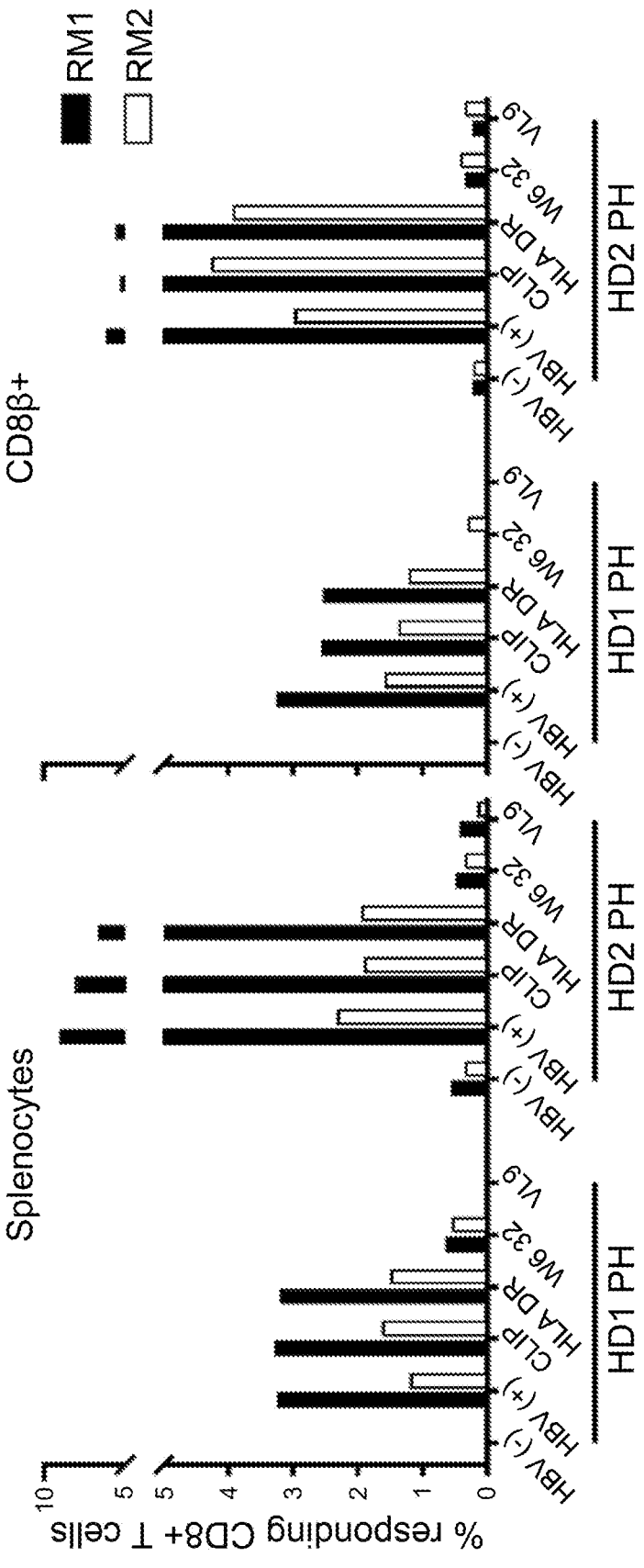

FIG. 3A shows the percent of HBV-specific CD8+ T cells restricted by MHC-I, MHC-II, and MHC-E in splenocytes and CD80-sorted effectors from RM1 and RM2 upon incubation with HBV-naïve or HBV-infected PH from two unrelated RM donors (RM8 and RM9). Responding T cells were identified by staining for CD3, CD8, and IFN-y. MHC restriction of the responding CD8+ T cells was identified with the following MHC blocking agents: W6/32 antibody (pan MHC-I), VL9 peptide (MHC-E), CLIP (MHC-II), or HLA-DR antibody (MHC-II). FIG. 3B shows the percent of HBV-specific CD8+ T cells restricted by MHC-I, MHC-II, and MHC-E from splenocytes or CD80-sorted effectors from RM1 and RM2 that were incubated with HBV-naïve or HBV-infected primary hepatocytes from human donors (HD1 and HD2). Responding CD8+ T cells were identified by CD3, Cd8, and IFN-7. MHC restriction of the responding CD8+ T cells was also identified with the following MHC blocking agents: W6/32 antibody (pan MHC-I), VL9 peptide (MHC-E), CLIP (MHC-II), or HLA-DR antibody (MHC-II).

Figures 4A, 4B:
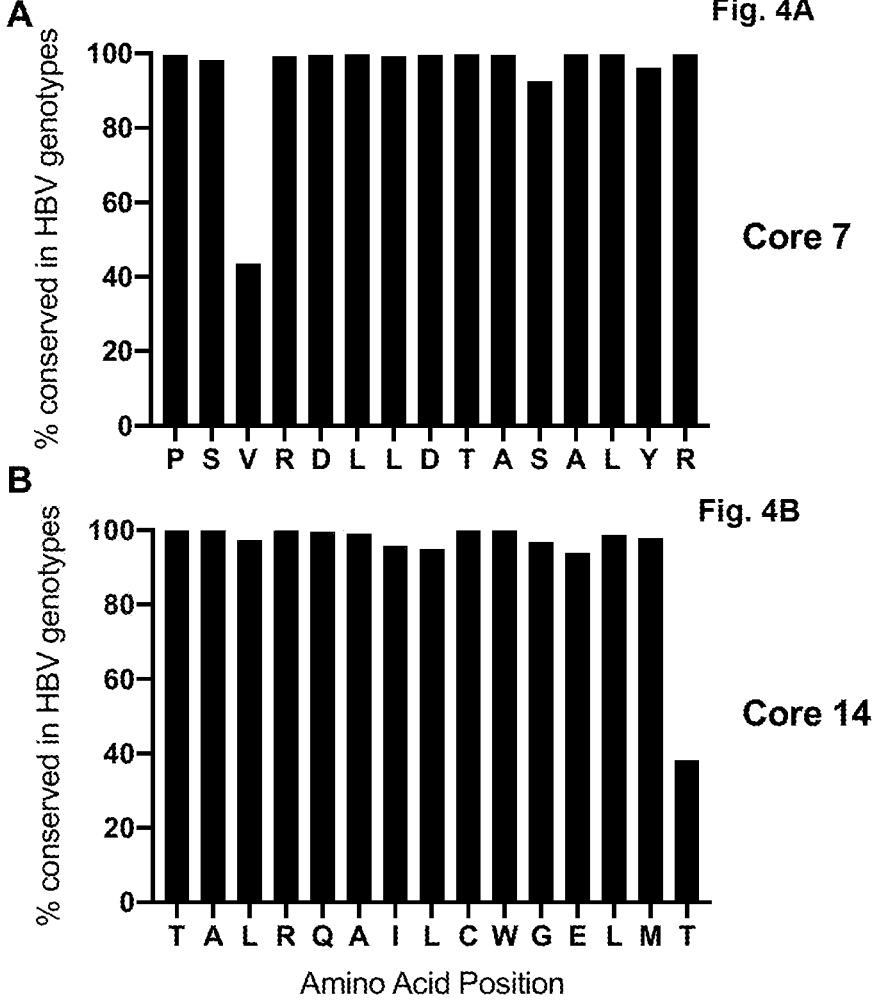

FIG. 4 is a bar graph showing the conservation of MHC-E-bound supertopes in HBV core antigen across global HBV strains. 6,203 full genome HBV sequences spanning all known HBV genotypes were translated and amino acids aligned against Core 7 (FIG. 4A) and Core 14 (FIG. 4B).

DETAILED DESCRIPTION OF THE
INVENTION

I. Terms

Unless otherwise noted, technical terms are used according to conventional usage.

All publications, patents, patent applications, internet sites, and accession numbers/database sequences (including both polynucleotide and polypeptide sequences) cited herein or listed in the Application Data Sheet, including U.S. Provisional Patent Applications No. 62/858,764 filed Jun. 7, 2019, are hereby incorporated by reference in their entirety for all purposes to the same extent as if each individual publication, patent, patent application, internet site, or accession number/database sequence were specifically and individually indicated to be so incorporated by reference.

Unless the context requires otherwise, throughout the present specification and claims, the word "comprise" and variations thereof, such as "comprises" and "comprising," are to be construed in an open, inclusive sense, that is, as "including, but not limited to". "Consisting of" shall mean excluding more than trace elements of other ingredients and substantial method steps disclosed herein. The term "consisting essentially of" limits the scope of a claim to the specified materials or steps, or to those that do not materially affect the basic characteristics of a claimed invention. For example, a composition consisting essentially of the elements as defined herein would not exclude trace contaminants from the isolation and purification method and pharmaceutically acceptable carriers, such as phosphate buffered saline, preservatives, and the like. Similarly, a protein consists essentially of a particular amino acid sequence when the protein includes additional amino acids that contribute to at most 20% of the length of the protein and do not substantially affect the activity of the protein (e.g., alters the activity of the protein by no more than 50%). Embodiments defined by each of the transitional terms are within the scope of this invention Although methods and materials similar or equivalent to those described herein may be used in the practice or testing of this disclosure, suitable methods and materials are described below. In addition, the materials, methods, and examples are illustrative only and not intended to be limiting. In order to facilitate review of the various embodiments of the disclosure, the following explanations of specific terms are provided.

Antigen: As used herein, the terms "antigen" or "immunogen" are used interchangeably to refer to a substance, typically a protein, which is capable of inducing an immune response in a subject. The term also refers to proteins that are immunologically active in the sense that once administered to a subject (either directly or by administering to the subject a nucleotide sequence or vector that encodes the protein) the protein is able to evoke an immune response of the humoral and/or cellular type directed against that protein.

Antigen-specific T cell: A CD8+ or CD4+ lymphocyte that recognizes a particular antigen. Generally, antigen-specific T cells specifically bind to a particular antigen presented by MHC molecules, but not other antigens presented by the same MHC.

Administration: As used herein, the term "administration" means to provide or give a subject an agent, such as a composition comprising an effective amount of a CMV vector comprising an exogenous antigen by any effective route. Exemplary routes of administration include, but are not limited to, injection (such as subcutaneous, intramuscular, intradermal, intraperitoneal, and intravenous), oral, sublingual, rectal, transdermal, intranasal, vaginal, and inhalation routes.

Effective amount: As used herein, the term "effective amount" refers to an amount of an agent, such as a CMV vector comprising a heterologous antigen or a transfected CD8+ T cell that recognizes a MHC-E/heterologous antigen-derived peptide complex, a MHC-II/heterologous antigen-derived peptide complex, or a MHC-I/heterologous antigen-derived peptide complex, that is sufficient to generate a desired response, such as reduce or eliminate a sign or symptom of a condition or disease or induce an immune response to an antigen. In some examples, an "effective amount" is one that treats (including prophylaxis) one or more symptoms and/or underlying causes of any of a disorder or disease. An effective amount may be a therapeutically effective amount, including an amount that prevents one or more signs or symptoms of a particular disease or condition from developing, such as one or more signs or symptoms associated with an infectious disease.

Heterologous antigen: As used herein, the term "heterologous antigen" refers to any protein or fragment thereof that is not derived from CMV. Heterologous antigens may be any antigen derived from HBV.

Immunogenic peptide: A peptide which comprises an allele-specific motif or other sequence, such as an N-terminal repeat, such that the peptide will bind an MHC molecule and induce a cytotoxic T lymphocyte ("CTL") response, or a B cell response (for example antibody production) against the antigen from which the immunogenic peptide is derived.

In one embodiment, immunogenic peptides are identified using sequence motifs or other methods, such as neural net or polynomial determinations known in the art. Typically, algorithms are used to determine the "binding threshold" of peptides to select those with scores that give them a high probability of binding at a certain affinity and will be immunogenic. The algorithms are based either on the effects on MHC binding of a particular amino acid at a particular position, the effects on antibody binding of a particular amino acid at a particular position, or the effects on binding of a particular substitution in a motif-containing peptide. Within the context of an immunogenic peptide, a "conserved residue" is one which appears in a significantly higher frequency than would be expected by random distribution at a particular position in a peptide. In one embodiment, a conserved residue is one where the MHC structure may provide a contact point with the immunogenic peptide.

Mutation: As used herein, the term "mutation" refers to any difference in a nucleic acid or polypeptide sequence from a normal, consensus, or "wild type" sequence. A mutant is any protein or nucleic acid sequence comprising a mutation. In addition, a cell or an organism with a mutation may also be referred to as a mutant. Some types of coding sequence mutations include point mutations (differences in individual nucleotides or amino acids); silent mutations (differences in nucleotides that do not result in an amino acid changes); deletions (differences in which one or more nucleotides or amino acids are missing, up to and including a deletion of the entire coding sequence of a gene); frameshift mutations (differences in which deletion of a number of nucleotides indivisible by 3 results in an alteration of the amino acid sequence). A mutation that results in a difference in an amino acid may also be called an amino acid substitution mutation. Amino acid substitution mutations may be described by the amino acid change relative to wild type at a particular position in the amino acid sequence.

Nucleotide sequences or nucleic acid sequences: The terms "nucleotide sequences" and "nucleic acid sequences" refer to deoxyribonucleic acid (DNA) or ribonucleic acid (RNA) sequences, including, without limitation, messenger RNA (mRNA), DNA/RNA hybrids, or synthetic nucleic acids. The nucleic acid may be single-stranded, or partially or completely double stranded (duplex). Duplex nucleic acids may be homoduplex or heteroduplex.

Operably Linked: As the term "operably linked" is used herein, a first nucleic acid sequence is operably linked with a second nucleic acid sequence when the first nucleic acid sequence is placed in such a way that it has an effect upon the second nucleic acid sequence. Operably linked DNA sequences may be contiguous, or they may operate at a distance.

Promoter: As used herein, the term "promoter" may refer to any of a number of nucleic acid control sequences that directs transcription of a nucleic acid. Typically, a eukaryotic promoter includes necessary nucleic acid sequences near the start site of transcription, such as, in the case of a polymerase II type promoter, a TATA element or any other specific DNA sequence that is recognized by one or more transcription factors. Expression by a promoter may be further modulated by enhancer or repressor elements. Numerous examples of promoters are available and well known to those of ordinary skill in the art. A nucleic acid comprising a promoter operably linked to a nucleic acid sequence that codes for a particular polypeptide may be termed an expression vector.

Recombinant: As used herein, the term "recombinant" with reference to a nucleic acid or polypeptide refers to one that has a sequence that is not naturally occurring or has a sequence that is made by an artificial combination of two or more otherwise separated segments of sequence, for example a CMV vector comprising a heterologous antigen. This artificial combination is often accomplished by chemical synthesis or, more commonly, by the artificial manipulation of isolated segments of nucleic acids, e.g., by genetic engineering techniques. A recombinant polypeptide may also refer to a polypeptide that has been made using recombinant nucleic acids, including recombinant nucleic acids transferred to a host organism that is not the natural source of the polypeptide (for example, nucleic acids encoding polypeptides that form a CMV vector comprising a heterologous antigen).

Pharmaceutically acceptable carriers: As used herein, a "pharmaceutically acceptable carrier" of use is conventional. Remington's Pharmaceutical Sciences, by E. W. Martin, Mack Publishing Co., Easton, PA, 19th Edition, 1995, describes compositions and formulations suitable for pharmaceutical delivery of the compositions disclosed herein. In general, the nature of the carrier will depend on the particular mode of administration being employed. For instance, parenteral formulations usually comprise injectable fluids that include pharmaceutically and physiologically acceptable fluids such as water, physiological saline, balanced salt solutions, aqueous dextrose, glycerol, or the like as a vehicle. For solid compositions (such as powder, pill, tablet, or capsule forms), conventional non-toxic solid carriers may include, for example, pharmaceutical grades of mannitol, lactose, starch, or magnesium stearate. In addition to biologically neutral carriers, pharmaceutical compositions to be administered may contain minor amounts of non-toxic auxiliary substances, such as wetting or emulsifying agents, preservatives, and pH buffering agents and the like, for example sodium acetate or sorbitan monolaurate.

Polynucleotide: As used herein, the term "polynucleotide" refers to a polymer of ribonucleic acid (RNA) or deoxyribonucleic acid (DNA). A polynucleotide is made up of four bases; adenine, cytosine, guanine, and thymine/uracil (uracil is used in RNA). A coding sequence from a nucleic acid is indicative of the sequence of the protein encoded by the nucleic acid.

Polypeptide: The terms "protein", "peptide", "polypeptide", and "amino acid sequence" are used interchangeably herein to refer to polymers of amino acid residues of any length. The polymer may be linear or branched, it may comprise modified amino acids or amino acid analogs, and it may be interrupted by chemical moieties other than amino acids. The terms also encompass an amino acid polymer that has been modified naturally or by intervention; for example, disulfide bond formation, glycosylation, lipidation, acetylation, phosphorylation, or any other manipulation or modification, such as conjugation with a labeling or bioactive component.

Orthologs of proteins are typically characterized by possession of greater than 75% sequence identity counted over the full-length alignment with the amino acid sequence of specific protein using ALIGN set to default parameters. Proteins with even greater similarity to a reference sequence will show increasing percentage identities when assessed by this method, such as at least 80%, at least 85%, at least 90%, at least 92%, at least 95%, or at least 98% sequence identity. In addition, sequence identity can be compared over the full length of particular domains of the disclosed peptides.

Sequence identity/similarity: As used herein, the identity/similarity between two or more nucleic acid sequences, or two or more amino acid sequences, is expressed in terms of the identity or similarity between the sequences. Sequence identity may be measured in terms of percentage identity; the higher the percentage, the more identical the sequences are. Sequence similarity may be measured in terms of percentage identity or similarity (which takes into account conservative amino acid substitutions); the higher the percentage, the more similar the sequences are. Polypeptides or protein domains thereof that have a significant amount of sequence identity and also function the same or similarly to one another (for example, proteins that serve the same functions in different species or mutant forms of a protein that do not change the function of the protein or the magnitude thereof) may be called "homologs."

Methods of alignment of sequences for comparison are well known in the art. Various programs and alignment algorithms are described in: Smith & Waterman, Adv Appl Math 2, 482 (1981); Needleman & Wunsch, J Mol Biol 48, 443 (1970); Pearson & Lipman, Proc Natl Acad Sci USA 85, 2444 (1988); Higgins & Sharp, Gene 73, 237-244 (1988); Higgins & Sharp, CABIOS 5, 151-153 (1989); Corpet et al., Nuc Acids Res 16, 10881-10890 (1988); Huang et al., Computer App Biosci 8, 155-165 (1992); and Pearson et al., Meth Mol Bio 24, 307-331 (1994). In addition, Altschul et al., J Mol Biol 215, 403-410 (1990), presents a detailed consideration of sequence alignment methods and homology calculations.

The NCBI Basic Local Alignment Search Tool (BLAST) (Altschul et al., (1990) supra) is available from several sources, including the National Center for Biological Information (NCBI, National Library of Medicine, Building 38A, Room 8N805, Bethesda, Md. 20894) and on the Internet, for use in connection with the sequence analysis programs blastp, blastn, blastx, tblastn and tblastx. Additional information may be found at the NCBI web site.

BLASTN is used to compare nucleic acid sequences, while BLASTP is used to compare amino acid sequences. If the two compared sequences share homology, then the designated output file will present those regions of homology as aligned sequences. If the two compared sequences do not share homology, then the designated output file will not present aligned sequences.

Once aligned, the number of matches is determined by counting the number of positions where an identical nucleotide or amino acid residue is presented in both sequences. The percent sequence identity is determined by dividing the number of matches either by the length of the sequence set forth in the identified sequence, or by an articulated length (such as 100 consecutive nucleotides or amino acid residues from a sequence set forth in an identified sequence), followed by multiplying the resulting value by 100. For example, a nucleic acid sequence that has 1166 matches when aligned with a test sequence having 1154 nucleotides is 75.0 percent identical to the test sequence (1166÷1554*100=75.0). The percent sequence identity value is rounded to the nearest tenth. For example, 75.11, 75.12, 75.13, and 75.14 are rounded down to 75.1, while 75.15, 75.16, 75.17, 75.18, and 75.19 are rounded up to 75.2. The length value will always be an integer. In another example, a target sequence containing a 20-nucleotide region that aligns with 20 consecutive nucleotides from an identified sequence as follows contains a region that shares 75 percent sequence identity to that identified sequence (that is, 15÷20*100=75).

For comparisons of amino acid sequences of greater than about 30 amino acids, the Blast 2 sequences function is employed using the default BLOSUM62 matrix set to default parameters, (gap existence cost of 11, and a per residue gap cost of 1). Homologs are typically characterized by possession of at least 70% sequence identity counted over the full-length alignment with an amino acid sequence using the NCBI Basic Blast 2.0, gapped blastp with databases such as the nr database, swissprot database, and patented sequences database. Queries searched with the blastn program are filtered with DUST (Hancock & Armstrong, Comput Appl Biosci 10, 67-70 (1994.) Other programs use SEG. In addition, a manual alignment may be performed. Proteins with even greater similarity will show increasing percentage identities when assessed by this method, such as at least about 75%, 80%, 85%, 90%, 95%, 98%, or 99% sequence identity to a protein.

When aligning short peptides (fewer than around 30 amino acids), the alignment is performed using the Blast 2 sequences function, employing the PAM30 matrix set to default parameters (open gap 9, extension gap 1 penalties). Proteins with even greater similarity to the reference sequence will show increasing percentage identities when assessed by this method, such as at least about 60%, 70%, 75%, 80%, 85%, 90%, 95%, 98%, or 99% sequence identity to a protein. When less than the entire sequence is being compared for sequence identity, homologs will typically possess at least 75% sequence identity over short windows of 10-20 amino acids, and may possess sequence identities of at least 85%, 90%, 95% or 98% depending on their identity to the reference sequence. Methods for determining sequence identity over such short windows are described at the NCBI web site.

One indication that two nucleic acid molecules are closely related is that the two molecules hybridize to each other under stringent conditions, as described above. Nucleic acid sequences that do not show a high degree of identity may nevertheless encode identical or similar (conserved) amino acid sequences, due to the degeneracy of the genetic code. Changes in a nucleic acid sequence may be made using this degeneracy to produce multiple nucleic acid molecules that all encode substantially the same protein. Such homologous nucleic acid sequences can, for example, possess at least about 50%, 60%, 70%, 80%, 90%, 95%, 98%, or 99% sequence identity to a nucleic acid that encodes a protein.

Subject: As used herein, the term "subject" refers to a living multi-cellular vertebrate organism, a category that includes both human and non-human mammals.

Supertope: As used herein, the term "supertope" or "supertope peptide" refers to a epitope or peptide that is recognized by T cells in greater than about 90% of the human population regardless of MHC haplotype, i.e., in the presence or absence of given MHC-I, MHC-II, or MHC-E alleles.

Treatment: As used herein, the term "treatment" refers to an intervention that ameliorates a sign or symptom of a disease or pathological condition. As used herein, the terms "treatment", "treat", and "treating," with reference to a disease, pathological condition or symptom, also refers to any observable beneficial effect of the treatment. The beneficial effect may be evidenced, for example, by a delayed onset of clinical symptoms of the disease in a susceptible subject, a reduction in severity of some or all clinical symptoms of the disease, a slower progression of the disease, a reduction in the number of relapses of the disease, an improvement in the overall health or well-being of the subject, or by other parameters well known in the art that are specific to the particular disease. A prophylactic treatment is a treatment administered to a subject who does not exhibit signs of a disease or exhibits only early signs, for the purpose of decreasing the risk of developing pathology. A therapeutic treatment is a treatment administered to a subject after signs and symptoms of the disease have developed.

Vaccine: An immunogenic composition that can be administered to a mammal, such as a human, to confer immunity, such as active immunity, to a disease or other pathological condition. Vaccines can be used prophylactically or therapeutically. Thus, vaccines can be used reduce the likelihood of developing a disease (such as a tumor or pathological infection) or to reduce the severity of symptoms of a disease or condition, limit the progression of the disease or condition (such as a tumor or a pathological infection), or limit the recurrence of a disease or condition (such as a tumor). In particular embodiments, a vaccine is a replication-deficient CMV expressing a HBV antigen.

Vector: Nucleic acid molecules of particular sequence can be incorporated into a vector that is then introduced into a host cell, thereby producing a transformed host cell. A vector may include nucleic acid sequences that permit it to replicate in a host cell, such as an origin of replication. A vector may also include one or more selectable marker genes and other genetic elements known in the art, including promoter elements that direct nucleic acid expression. Vectors can be viral vectors, such as CMV vectors. Viral vectors may be constructed from wild type or attenuated virus, including replication deficient virus.

II. Methods for the Treatment and Prevention of Hepatitis B Infection

Disclosed herein are methods for the treatment or prevention of hepatitis B virus infection. The methods involve administering an effective amount of at least one recombinant CMV vector comprising at least one heterologous antigen to a subject, wherein the at least one heterologous antigen comprises an antigen derived from the hepatitis B virus.

The antigen derived from the hepatitis B virus may be derived from any portion of the viral pathogen. Hepatitis B antigens include, but are not limited to, the core protein, envelope protein, surface proteins, X protein, and polymerase protein.

In some embodiments, the CMV vector does not express an active UL128, UL130, UL146, and UL147 protein due to the presence of a mutation in the nucleic acid sequence encoding UL128, UL130, UL146, and UL147 or homologs thereof, or orthologs thereof (homologous genes of CMV that infect other species). The mutation may be any mutation that results in a lack of expression of active proteins. Such mutations may include point mutations, frameshift mutations, deletions of less than all of the sequence that encodes the protein (truncation mutations), or deletions of all of the nucleic acid sequence that encodes the protein, or any other mutations.

In further examples, the CMV vector does not express an active UL128, UL130, UL146, and UL147 protein due to the presence of a nucleic acid sequence in the vector that comprises an antisense or RNAi sequence (siRNA or miRNA) that inhibits the expression of the UL128, UL130, UL146, and UL147 proteins. Mutations and/or antisense and/or RNAi may be used in any combination to generate a CMV vector lacking active UL128, UL130, UL146, and UL147.

In some embodiments, the CD8+ T cell response elicited by this vector is characterized by having at least 10% of the CD8+ T cells directed against HBV epitopes presented by MHC-E. In further examples, at least 15%, at least 20%, at least 30%, at least 40%, at least 50%, at least 60%, at least 75%, at least 90%, or at least 95% of the CD8+ T cells are restricted by MHC-E. In some embodiments, the HBV-specific CD8+ T cells restricted by MHC-E recognize peptides shared by at least 90% of other subjects immunized with the vector. In some embodiments, the CD8+ T cells are directed against a HBV supertope presented by MHC-E. In some embodiments, the CD8+ T cell response elicited by this vector is characterized by having at least 10% of the CD8+ T cells directed against epitopes presented by MHC-II. In further examples, at least 15%, at least 20%, at least 30%, at least 40%, at least 50%, at least 60%, at least 75%, at least 90%, or at least 95% of the CD8+ T cells are restricted by MHC-II. In some embodiments, the HBV-specific CD8+ T cells restricted by MHC-II recognize HBV peptides shared by at least 90% of other subjects immunized with the vector. In some embodiments, the HBV-specific CD8+ T cells are directed against a HBV supertope presented by MHC-II.

In some embodiments, the method further comprises identifying a CD8+ T cell receptor from the CD8+ T cells elicited by the CMV vector, wherein the CD8+ T cell receptor recognizes a MHC-E/HBV antigen-derived peptide complex. In some embodiments, the CD8+ T cell receptor is identified by RNA or DNA sequencing. In some embodiments, the method further comprises a CD8+ T cell receptor that recognizes MHC-E supertopes of HBV.

In some embodiments, the method further comprises identifying a CD8+ T cell receptor from the CD8+ T cells elicited by the CMV vector, wherein the CD8+ T cell receptor recognizes a MHC-II/HBV antigen-derived peptide complex. In some embodiments, the CD8+ T cell receptor is identified by RNA or DNA sequencing. In some embodiments, the method further comprises a CD8+ T cell receptor that recognizes MHC-II supertopes of HBV.

Also disclosed herein is a method of generating CD8+ T cells that recognize MHC-E-HBV peptide complexes. This method involves administering to a first subject (or animal) a CMV vector in an amount effective to generate a set of CD8+ T cells that recognize MHC-E/HBV peptide complexes. In some embodiments, the CMV vector comprises a first nucleic acid sequence encoding at least one HBV antigen and does not express an active UL128, UL130, UL146, and UL147 proteins or orthologs thereof. In some embodiments, the HBV antigens can be hepatitis B virus core, envelope, surface, or polymerase antigens.

This method further comprises: identifying a first CD8+ T cell receptor from the set of CD8+ T cells, wherein the first CD8+ T cell receptor recognizes an MHC-E/HBV antigen-derived peptide complex. In some embodiments, the first CD8+ T cell receptor is identified by DNA or RNA sequencing. In some embodiments, this method can further comprise transfecting the one or more CD8+ T cells with an expression vector, wherein the expression vector comprises a nucleic acid sequence encoding a second CD8+ T cell receptor and a promoter operably linked to the nucleic acid sequence encoding the T cell receptor, wherein the second CD8+ T cell receptor comprises CDR3α and CDR3β of the first CD8+ T cell receptor, thereby generating one or more transfected CD8+ T cells that recognize a MHC-E/HBV antigen-derived peptide complex. The one or more CD8+ T cells for transfection with the expression vector may be isolated from the first subject or a second subject.

In some embodiments, the method further comprises identifying a CD8+ T cell receptor from the CD8+ T cells elicited by the CMV vector, wherein the CD8+ T cell receptor recognizes an MHC-E/HBV antigen-derived peptide complex. In some embodiments, the CD8+ T cell receptor is identified by RNA or DNA sequencing. In some embodiments, the method further comprises an HBV-specific CD8+ T cell receptor that recognizes MHC-E supertopes.

Also disclosed is a transfected CD8+ T cell that recognizes MHC-E-HBV peptide complexes prepared by a process comprising the steps of: (1) administering to a first subject a CMV vector in an amount effective to generate a set of CD8+ T cells that recognize MHC-E/HBV peptide complexes, wherein the recombinant CMV vector comprises at least one HBV antigen; (2) identifying a first CD8+ T cell receptor from the set of CD8+ T cells, wherein the first CD8+ T cell receptor recognizes a MHC-E/HBV antigen-derived peptide complex; (3) isolating one or more CD8+ T cells from the first subject or a second subject; and (4) transfecting the one or more CD8+ T cells isolated from the first or second subject with an expression vector, thereby creating a transfected T cell that recognizes MHC-E-HBV peptide complexes. The CMV vector comprises a first nucleic acid sequence encoding at least one HBV antigen and does not express an active UL128, UL130, UL146, and UL147 protein or ortholog thereof. The expression vector comprises a nucleic acid sequence encoding a second CD8+ T cell receptor and a promoter operably linked to the nucleic acid sequence encoding the second CD8+ T cell receptor, wherein the second CD8+ T cell receptor comprises CDR3α and CDR3β of the first CD8+ T cell receptor. The hepatitis B antigens may be hepatitis B virus core, envelope, surface, or polymerase antigens.

In some embodiments, the CD8+ T cell response elicited by the CMV vector is characterized by having at least 10% of the CD8+ T cells directed against HBV epitopes presented by MHC-II. In further examples, at least 15%, at least 20%, at least 30%, at least 40%, at least 50%, at least 60%, at least 75%, at least 90%, at least 95% or at least 95% of the CD8+ T cells are restricted by MHC-II. In some embodiments, the CD8+ T cells restricted by MHC-II recognize HBV peptides shared by at least 90% of other subjects immunized with the vector. In some embodiments, the CD8+ T cells are directed against a HBV supertope presented by MHC-II.

In some embodiments, the method further comprises identifying a CD8+ T cell receptor from the CD8+ T cells elicited by the CMV/HBV vector, wherein the CD8+ T cell receptor recognizes a MHC-II/HBV antigen-derived peptide complex. In some embodiments, the CD8+ T cell receptor is identified by RNA or DNA sequencing. In some embodiments, the method further comprises a CD8+ T cell receptor that recognizes MHC-II-restricted HBV supertopes.

Human or animal CMV vectors, when used as expression vectors, are innately non-pathogenic in the selected subjects such as humans. In some embodiments, the CMV vectors have been modified to render them non-pathogenic (incapable of within host or host-to-host spread) in the selected subjects.

A HBV antigen, as described herein, may be any HBV protein or fragment thereof.

The recombinant CMV vectors disclosed herein may be derived from human cytomegalovirus vectors, rhesus macaque cytomegalovirus vectors, or cynomolgus macaque vectors.

The recombinant CMV vectors disclosed herein may be used as an immunogenic, immunological or vaccine composition containing the recombinant CMV virus or vector, and a pharmaceutically acceptable carrier or diluent. An immunological composition containing the recombinant CMV virus or vector (or an expression product thereof) elicits an immunological response—local or systemic. The response can, but need not be, protective. An immunogenic composition containing the recombinant CMV virus or vector (or an expression product thereof) likewise elicits a local or systemic immunological response which can, but need not be, protective. A vaccine composition elicits a local or systemic protective response. Accordingly, the terms
"immunological composition" and "immunogenic compo-
sition" include a "vaccine composition" (as the two former
terms may be protective compositions).

The recombinant CMV vectors disclosed herein may be
used in methods of inducing an immunological response in
a subject comprising administering to the subject an immu-
nogenic, immunological or vaccine composition comprising
the recombinant CMV virus or vector and a pharmaceuti-
cally acceptable carrier or diluent.

The CMV vectors disclosed herein may be used in thera-
peutic compositions containing the recombinant CMV virus
or vector and a pharmaceutically acceptable carrier or
diluent. The CMV vectors disclosed herein may be prepared
by inserting DNA comprising a sequence that encodes the
HBV antigen into an essential or non-essential region of the
CMV genome. The method may further comprise deleting
one or more regions from the CMV genome. The method
may comprise in vivo recombination. Thus, the method may
comprise transfecting a cell with CMV DNA in a cell-
compatible medium in the presence of donor DNA compris-
ing the heterologous DNA flanked by DNA sequences
homologous with portions of the CMV genome, whereby the
heterologous DNA is introduced into the genome of the
CMV, and optionally then recovering CMV modified by the
in vivo recombination. The method may also comprise
cleaving CMV DNA to obtain cleaved CMV DNA, ligating
the heterologous DNA to the cleaved CMV DNA to obtain
hybrid CMV-heterologous DNA, transfecting a cell with the
hybrid CMV-heterologous DNA, and optionally then recov-
ering CMV modified by the presence of the HBV DNA.
Since in vivo recombination is comprehended, the method
accordingly also provides a plasmid comprising donor DNA
not naturally occurring in CMV encoding a polypeptide
foreign to CMV, the donor DNA is within a segment of
CMV DNA that would otherwise be co-linear with an
essential or non-essential region of the CMV genome such
that DNA from an essential or nonessential region of CMV
is flanking the donor DNA The HBV DNA may be inserted
into CMV to generate the recombinant CMV in any orien-
tation that yields stable integration of that DNA, and expres-
sion thereof, when desired.

The DNA encoding the HBV antigen in the recombinant
CMV vector may also include a promoter. The promoter
may be from any source such as a herpes virus, including an
endogenous cytomegalovirus (CMV) promoter, such as a
human CMV (HCMV), rhesus macaque CMV (RhCMV),
murine, or other CMV promoter. The promoter may also be
a nonviral promoter such as the EF1α promoter. The pro-
moter may be a truncated transcriptionally active promoter
which comprises a region transactivated with a transactivat-
ing protein provided by the virus and the minimal promoter
region of the full-length promoter from which the truncated
transcriptionally active promoter is derived. The promoter
may be composed of an association of DNA sequences
corresponding to the minimal promoter and upstream regu-
latory sequences. A minimal promoter is composed of the
CAP site plus ATA box (minimum sequences for basic level
of transcription; unregulated level of transcription);
"upstream regulatory sequences" are composed of the
upstream element(s) and enhancer sequence(s). Further, the
term "truncated" indicates that the full-length promoter is
not completely present, i.e., that some portion of the full-
length promoter has been removed. And, the truncated
promoter may be derived from a herpesvirus such as MCMV
or HCMV, e.g., HCMV-IE or MCMV-IE. There may be up
to a 40% and even up to a 90% reduction in size, from a full-length promoter, based upon base pairs. The promoter
may also be a modified non-viral promoter. As to HCMV
promoters, reference is made to U.S. Pat. Nos. 5,168,062
and 5,385,839. As to transfecting cells with plasmid DNA
for expression therefrom, reference is made to Feigner et al.
(1994), *J Biol. Chem.* 269, 2550-2561. And, as to direct
injection of plasmid DNA as a simple and effective method
of vaccination against a variety of infectious diseases ref-
erence is made to *Science,* 259:1745-49, 1993. It is therefore
within the scope of this disclosure that the vector may be
used by the direct injection of vector DNA.

Also disclosed is an expression cassette that may be
inserted into a recombinant virus or plasmid comprising the
truncated transcriptionally active promoter. The expression
cassette may further include a functional truncated polyade-
nylation signal; for instance an SV40 polyadenylation signal
which is truncated, yet functional. Considering that nature
provided a larger signal, it is indeed surprising that a
truncated polyadenylation signal is functional. A truncated
polyadenylation signal addresses the insert size limit prob-
lems of recombinant viruses such as CMV. The expression
cassette may also include HBV DNA with respect to the
virus or system into which it is inserted; and that DNA may
be HBV DNA as described herein.

As to HBV antigens for use in vaccine or immunological
compositions, see also *Stedman's Medical Dictionary* (24th
edition, 1982, e.g., definition of vaccine (for a list of
antigens used in vaccine formulations); such antigens or
epitopes of interest from those antigens may be used. As to
HBV antigens, one skilled in the art may select an antigen
and the coding DNA therefor from the knowledge of the
amino acid and corresponding DNA sequences of the pep-
tide or polypeptide, as well as from the nature of particular
amino acids (e.g., size, charge, etc.) and the codon diction-
ary, without undue experimentation. Exemplary antigens
include, but are not limited to, a hepatitis B virus core,
envelope, surface, X, or polymerase antigen.

One method to determine T epitopes of a HBV antigen
involves epitope mapping. Overlapping peptides of the
heterologous antigen are generated by oligo-peptide synthe-
sis. The individual peptides are then tested for their ability
to bind to an antibody elicited by the native protein or to
induce T cell or B cell activation. This approach has been
particularly useful in mapping T cell epitopes since the T cell
recognizes short linear peptides complexed with MHC mol-
ecules.

An immune response to a HBV antigen is generated, in
general, as follows: T cells recognize proteins only when the
protein has been cleaved into smaller peptides and is pre-
sented in a complex called the "major histocompatibility
complex (MHC)" located on another cell's surface. There
are two classes of MHC complexes—class I and class II, and
each class is made up of many different alleles. Different
species, and individual subjects have different types of MHC
complex alleles; they are said to have a different MHC type.
One type of MHC class I molecule is called MHC-E
(HLA-E in humans, Mamu-E in RM, Qa-lb in mice).

It is noted that the DNA comprising the sequence encod-
ing the HBV antigen may itself include a promoter for
driving expression in the CMV vector or the DNA may be
limited to the coding DNA of the heterologous antigen. This
construct may be placed in such an orientation relative to an
endogenous CMV promoter that it is operably linked to the
promoter and is thereby expressed. Further, multiple copies
of DNA encoding the heterologous antigen or use of a strong
or early promoter or early and late promoter, or any com-
bination thereof, may be done so as to amplify or increase expression. Thus, the DNA encoding the heterologous antigen may be suitably positioned with respect to a CMV endogenous promoter, or those promoters may be translocated to be inserted at another location together with the DNA encoding the heterologous antigen. Nucleic acids encoding more than one heterologous antigen may be packaged in the CMV vector.

Further disclosed are pharmaceutical and other compositions containing the disclosed CMV vectors. Such pharmaceutical and other compositions may be formulated so as to be used in any administration procedure known in the art. Such pharmaceutical compositions may be via a parenteral route (intradermal, intramuscular, subcutaneous, intravenous, or others). The administration may also be via a mucosal route, e.g., oral, nasal, genital, etc.

The disclosed pharmaceutical compositions may be prepared in accordance with standard techniques well known to those skilled in the pharmaceutical arts. Such compositions may be administered in dosages and by techniques well known to those skilled in the medical arts taking into consideration such factors as the breed or species, age, sex, weight, and condition of the particular patient, and the route of administration. The compositions may be administered alone, or may be co-administered or sequentially administered with other CMV vectors or with other immunological, antigenic or vaccine or therapeutic compositions. Such other compositions may include purified native antigens or epitopes or antigens or epitopes from the expression by a recombinant CMV or another vector system; and are administered taking into account the aforementioned factors.

Examples of compositions include liquid preparations for orifice, e.g., oral, nasal, anal, genital, e.g., vaginal, etc., administration such as suspensions, syrups, or elixirs; and, preparations for parenteral, subcutaneous, intradermal, intramuscular, or intravenous administration (e.g., injectable administration) such as sterile suspensions or emulsions. In such compositions the recombinant may be in admixture with a suitable carrier, diluent, or excipient such as sterile water, physiological saline, glucose or the like.

Antigenic, immunological or vaccine compositions typically may contain an adjuvant and an amount of the CMV vector or expression product to elicit the desired response. In human applications, alum (aluminum phosphate or aluminum hydroxide) is a typical adjuvant. Saponin and its purified component Quil A, Freund's complete adjuvant and other adjuvants used in research and veterinary applications have toxicities which limit their potential use in human vaccines. Chemically defined preparations such as muramyl dipeptide, monophosphoryllipid A, phospholipid conjugates such as those described by Goodman-Snitkoff et al., *J Immunol.* 147:410-415 (1991), encapsulation of the protein within a proteoliposome as described by Miller et al., *J Exp. Med.* 176:1739-1744 (1992), and encapsulation of the protein in lipid vesicles such as Novasome lipid vesicles (Micro Vescular Systems, Inc., Nashua, N.H.) may also be used.

The composition may be packaged in a single dosage form for immunization by parenteral (e.g., intramuscular, intradermal or subcutaneous) administration or orifice administration, e.g., perlingual (e.g., oral), intragastric, mucosal including intraoral, intraanal, intravaginal, and the like administration. And again, the effective dosage and route of administration are determined by the nature of the composition, by the nature of the expression product, by expression level if recombinant CMV is directly used, and by known factors, such as breed or species, age, sex, weight, condition and nature of host, as well as $LD_{50}$ and other screening procedures which are known and do not require undue experimentation. Dosages of expressed product may range from a few to a few hundred micrograms, e.g., 5 to 500 μg. The CMV vector may be administered in any suitable amount to achieve expression at these dosage levels. In nonlimiting examples: CMV vectors may be administered in an amount of at least $10^2$ pfu; thus, CMV vectors may be administered in at least this amount; or in a range from about $10^2$ pfu to about $10^7$ pfu. Other suitable carriers or diluents may be water or a buffered saline, with or without a preservative. The CMV vector may be lyophilized for resuspension at the time of administration or may be in solution. "About" may mean within 1%, 5%, 10% or 20% of a defined value.

It should be understood that the proteins and the nucleic acids encoding them of the present disclosure may differ from the exact sequences illustrated and described herein. Thus, the disclosure contemplates deletions, additions, truncations, and substitutions to the sequences shown, so long as the sequences function in accordance with the methods of the disclosure. In this regard, substitutions will generally be conservative in nature, i.e., those substitutions that take place within a family of amino acids. For example, amino acids are generally divided into four families: (1) acidic—aspartate and glutamate; (2) basic—lysine, arginine, and histidine; (3) nonpolar—alanine, valine, leucine, isoleucine, proline, phenylalanine, methionine, and tryptophan; and (4) uncharged polar—glycine, asparagine, glutamine, cysteine, serine threonine, and tyrosine. Phenylalanine, tryptophan, and tyrosine are sometimes classified as aromatic amino acids. It is reasonably predictable that an isolated replacement of leucine with isoleucine or valine, or vice versa; an aspartate with a glutamate or vice versa; a threonine with a serine or vice versa; or a similar conservative replacement of an amino acid with a structurally related amino acid, will not have a major effect on the biological activity. Proteins having substantially the same amino acid sequence as the proteins described but possessing minor amino acid substitutions that do not substantially affect the immunogenicity of the protein are, therefore, within the scope of the disclosure.

The nucleotide sequences of the present disclosure may be codon optimized, for example the codons may be optimized for use in human cells. For example, any viral or bacterial sequence may be so altered. Many viruses, including HIV and other lentiviruses, use a large number of rare codons and, by altering these codons to correspond to codons commonly used in the desired subject, enhanced expression of the heterologous antigen may be achieved as described in Andre et al., *J Virol.* 72:1497-1503, 1998.

Nucleotide sequences encoding functionally and/or antigenically equivalent variants and derivatives of the CMV vectors and the glycoproteins included therein are contemplated. These functionally equivalent variants, derivatives, and fragments display the ability to retain antigenic activity. For instance, changes in a DNA sequence that do not change the encoded amino acid sequence, as well as those that result in conservative substitutions of amino acid residues, one or a few amino acid deletions or additions, and substitution of amino acid residues by amino acid analogs are those which will not significantly affect properties of the encoded polypeptide. Conservative amino acid substitutions are glycine/alanine; valine/isoleucine/leucine; asparagine/glutamine; aspartic acid/glutamic acid; serine/threonine/methionine; lysine/arginine; and phenylalanine/tyrosine/tryptophan. In one embodiment, the variants have at least 50%, at least 55%, at least 60%, at least 65%, at least 70%, at least 75%, at least 80%, at least 85%, at least 86%, at least 87%, at least 88%, at least 89%, at least 90%, at least 91%, at least 92%, at least 93%, at least 94%, at least 95%, at least 96%, at least 97%, at least 98%, or at least 99% homology or identity to the antigen, epitope, immunogen, peptide, or polypeptide of interest.

Sequence identity or homology is determined by comparing the sequences when aligned so as to maximize overlap and identity while minimizing sequence gaps. In particular, sequence identity may be determined using any of a number of mathematical algorithms. A nonlimiting example of a mathematical algorithm used for comparison of two sequences is the algorithm of Karlin & Altschul, *Proc. Natl. Acad. Sci. USA* 1990; 87: 2264-2268, modified as in Karlin & Altschul, *Proc. Natl. Acad. Sci. USA* 1993; 90: 5873-5877.

Another example of a mathematical algorithm used for comparison of sequences is the algorithm of Myers & Miller, *CABIOS* 1988; 4: 11-17. Such an algorithm is incorporated into the ALIGN program (version 2.0) which is part of the GCG sequence alignment software package. When utilizing the ALIGN program for comparing amino acid sequences, a PAM120 weight residue table, a gap length penalty of 12, and a gap penalty of 4 may be used. Yet another useful algorithm for identifying regions of local sequence similarity and alignment is the FASTA algorithm as described in Pearson & Lipman, *Proc. Nat. Acad. Sci. USA* 1988; 85: 2444-2448.

Advantageous for use according to the present disclosure is the WU-BLAST (Washington University BLAST) version 2.0 software. WU-BLAST version 2.0 executable programs for several UNIX platforms may be downloaded from ftp://blast.wustl.edu/blast/executables. This program is based on WU-BLAST version 1.4, which in turn is based on the public domain NCBI-BLAST version 1.4 (Altschul & Gish, 1996, Local alignment statistics, Doolittle ed., *Methods in Enzymology* 266: 460-480; Altschul et al., *Journal of Molecular Biology* 1990; 215: 403-410; Gish & States, 1993; *Nature Genetics* 3: 266-272; Karlin & Altschul, 1993; *Proc. Natl. Acad. Sci. USA* 90: 5873-5877; all of which are incorporated by reference herein).

The various recombinant nucleotide sequences and antibodies and/or antigens of the disclosure are made using standard recombinant DNA and cloning techniques. Such techniques are well known to those of skill in the art. See for example, "*Molecular Cloning: A Laboratory Manual*", second edition (Sambrook et al. 1989).

The nucleotide sequences of the present disclosure may be inserted into "vectors." The term "vector" is widely used and understood by those of skill in the art, and as used herein the term "vector" is used consistent with its meaning to those of skill in the art. For example, the term "vector" is commonly used by those skilled in the art to refer to a vehicle that allows or facilitates the transfer of nucleic acid molecules from one environment to another or that allows or facilitates the manipulation of a nucleic acid molecule.

Any vector that allows expression of the viruses of the present disclosure may be used in accordance with the present disclosure. In certain embodiments, the disclosed viruses may be used in vitro (such as using cell-free expression systems) and/or in cultured cells grown in vitro in order to produce the encoded heterologous antigen (e.g., pathogen-specific antigens, HIV antigens, hepatitis B antigens, and antibodies) which may then be used for various applications such as in the production of proteinaceous vaccines. For such applications, any vector that allows expression of the virus in vitro and/or in cultured cells may be used.

For the disclosed heterologous antigens to be expressed, the protein coding sequence of the heterologous antigen should be "operably linked" to regulatory or nucleic acid control sequences that direct transcription and translation of the protein. As used herein, a coding sequence and a nucleic acid control sequence or promoter are said to be "operably linked" when they are covalently linked in such a way as to place the expression or transcription and/or translation of the coding sequence under the influence or control of the nucleic acid control sequence. The "nucleic acid control sequence" may be any nucleic acid element, such as, but not limited to promoters, enhancers, IRES, introns, and other elements described herein that direct the expression of a nucleic acid sequence or coding sequence that is operably linked thereto. The term "promoter" will be used herein to refer to a group of transcriptional control modules that are clustered around the initiation site for RNA polymerase II and that when operationally linked to the protein coding sequences of the disclosure lead to the expression of the encoded protein. The expression of the transgenes of the present disclosure may be under the control of a constitutive promoter or of an inducible promoter, which initiates transcription only when exposed to some particular external stimulus, such as, without limitation, antibiotics such as tetracycline, hormones such as ecdysone, or heavy metals. The promoter may also be specific to a particular cell-type, tissue, or organ. Many suitable promoters and enhancers are known in the art, and any such suitable promoter or enhancer may be used for expression of the transgenes of the disclosure. For example, suitable promoters and/or enhancers may be selected from the Eukaryotic Promoter Database (EPDB).

The vectors used in accordance with the present disclosure may contain a suitable gene regulatory region, such as a promoter or enhancer, such that the antigens of the disclosure may be expressed.

The CMV vectors described herein may contain mutations that may prevent host to host spread, thereby rendering the virus unable to infect immunocompromised or other subjects that could face complications as a result of CMV infection. The CMV vectors described herein may also contain mutations that result in the presentation of immunodominant and nonimmunodominant epitopes as well as non-canonical MHC restriction. However, mutations in the CMV vectors described herein do not affect the ability of the vector to reinfect a subject that has been previously infected with CMV. Such CMV mutations are described in, for example, US Patent Publications 2013-013676S; 2010-0142S23; 2014-014103S; and PCT application publication WO 2014/13S209, all of which are incorporated by reference herein.

The disclosed CMV vectors may be administered in vivo, for example where the aim is to produce an immunogenic response, including a CD8+ immune response, including an immune response characterized by a high percentage of the CD8+ T cell response being restricted by MHC-E or MHC-II (or a homolog or ortholog thereof). For example, in some examples it may be desired to use the disclosed CMV vectors in a laboratory animal, such as rhesus macaques for preclinical testing of immunogenic compositions and vaccines using RhCMV. In other examples, it will be desirable to use the disclosed CMV vectors in human subjects, such as in clinical trials and for actual clinical use of the immunogenic compositions using HCMV.

For such in vivo applications the disclosed CMV vectors are administered as a component of an immunogenic composition further comprising a pharmaceutically acceptable carrier. In some embodiments, the immunogenic compositions of the disclosure are useful to stimulate an immune response against the heterologous antigen, including a pathogen-specific antigen and may be used as one or more components of a prophylactic or therapeutic vaccine against pathogen-specific antigens for the prevention, amelioration, or treatment of a pathogenic infection. The nucleic acids and vectors of the disclosure are particularly useful for providing genetic vaccines, i.e., vaccines for delivering the nucleic acids encoding the antigens of the disclosure to a subject, such as a human, such that the antigens are then expressed in the subject to elicit an immune response.

Immunization schedules (or regimens) are well known for animals (including humans) and may be readily determined for the particular subject and immunogenic composition. Hence, the immunogens may be administered one or more times to the subject. Preferably, there is a set time interval between separate administrations of the immunogenic composition. While this interval varies for every subject, typically it ranges from 10 days to several weeks, [and is often 2, 4, 6, or 8 weeks. For humans, the interval is typically from 2 to 6 weeks. In a particularly advantageous embodiment of the present disclosure, the interval is longer, advantageously about 10 weeks, 12 weeks, 14 weeks, 16 weeks, 18 weeks, 20 weeks, 22 weeks, 24 weeks, 26 weeks, 28 weeks, 30 weeks, 32 weeks, 34 weeks, 36 weeks, 38 weeks, 40 weeks, 42 weeks, 44 weeks, 46 weeks, 48 weeks, 50 weeks, 52 weeks, 54 weeks, 56 weeks, 58 weeks, 60 weeks, 62 weeks, 64 weeks, 66 weeks, 68 weeks, or 70 weeks. The immunization regimes typically have from 1 to 6 administrations of the immunogenic composition, but may have as few as one or two or four. The methods of inducing an immune response may also include administration of an adjuvant with the immunogens. In some instances, annual, biannual or other long interval (5-10 years) booster immunization may supplement the initial immunization protocol. The present methods also include a variety of prime-boost regimens. In these methods, one or more priming immunizations are followed by one or more boosting immunizations. The actual immunogenic composition may be the same or different for each immunization and the type of immunogenic composition (e.g., containing protein or expression vector), the route, and formulation of the immunogens may also be varied. For example, if an expression vector is used for the priming and boosting steps, it may either be of the same or different type (e.g., DNA or bacterial or viral expression vector). One useful prime-boost regimen provides for two priming immunizations, four weeks apart, followed by two boosting immunizations at 4 and 8 weeks after the last priming immunization. It should also be readily apparent to one of skill in the art that there are several permutations and combinations that are encompassed using the DNA, bacterial and viral expression vectors of the disclosure to provide priming and boosting regimens. CMV vectors may be used repeatedly while expressing different antigens derived from different pathogens.

EXAMPLES

Example 1: RHCMV/HBV Inoculated Rhesus Macaques Mount MHC-E Restricted Cd8+ T Cell Responses Against HBV Antigens RhCMV strain 68-1 vectors engineered to express antigenic targets elicit broad, effector-memory CD8+ T cell responses restricted either by the non-classical molecule MHC-E, a monomorphic MHC class lb molecule normally involved in NK cell signaling, or MHC-II. RhCMV vaccine vectors expressing simian immunodeficiency virus (SIV)

antigens protect 50% of RM following repeated low-dose intrarectal and intravaginal challenge with the highly pathogenic strain SIVmac239.

Here, it was determined whether RhCMV/HBV-induced, unconventionally restricted CD8+ T cell responses recognize HBV-infected hepatocytes. Targeting of these unique CD8+ T cell restriction molecules would constitute a new paradigm for the treatment of HBV infection and theoretically could be universally applied to all patients given the extreme conservation of MHC-E across humans and macaques (Wu et al. 2018. The Role of MHC-E in T Cell Immunity Is Conserved among Humans, Rhesus Macaques, and Cynomolgus Macaques. J. Immunol. 200: 49-60).

Four rhesus macaques (RM) were inoculated with strain 68-1 RhCMV expressing HBV genotype D serotype ayw core, surface, and/or polymerase antigens. Genotype D, serotype ayw HBV core, polymerase, and S Ag gene fragments were isolated by PCR from previously described plasmids (Frank Chisari, Scripps Research Institute). The N-terminal 333 amino acids of polymerase obtained from plasmid pCDNA3-POL/ENV (Kakimi, K. et al. 2002. Immunogenicity and tolerogenicity of hepatitis B virus structural and nonstructural proteins: implications for immunotherapy of persistent viral infections. J. Virol. 76: 8609-8620) were C-terminally HA-epitope tagged and fused by PCR-mediated mutagenesis to the C-terminal 228 amino acids of the S Ag obtained from plasmid pCMV-S2/S (Michel, M. L., et al. 1995. DNA-mediated immunization to the hepatitis B surface antigen in mice: aspects of the humoral response mimic hepatitis B viral infection in humans. Proc. Natl. Acad. Sci. USA 92: 5307-5311.) to generate fusion S/PolN (left forward primer: 59-CATCG-AGCTAGCACCATGGAGAACATCACATCAGG-39 (SEQ ID NO: 1), left reverse primer: 59-GTGTTGATAG-GATAGGGGAATGTATACCCAAAGAC-39 (SEQ ID NO: 2); right forward primer: 59-GTCTTTGGGTATACAT-TCCCCTATCCTATCAACAC-39 (SEQ ID NO: 3), right reverse primer: 59-GGAATCGTCGACTCAAGCGTA-ATCTGGAACATCGTATGGGTAAAGATTGACG ATA-AGGGAGAGGCAG-39 (SEQ ID NO: 4)). The final PCR product was blunt-end cloned into either pJet vector (Thermo Fisher Scientific) to be a template for bacterial artificial chromosome (BAC) recombineering or into pORI to evaluate expression. The C-terminal 416 amino acids of polymerase obtained from plasmid pCDNA3-POL/ENV (Kakimi, K. et al. 2002. Immunogenicity and tolerogenicity of hepatitis B virus structural and nonstructural proteins: implications for immunotherapy of persistent viral infections. J. Virol. 76: 8609-8620) was HA-epitope tagged by PCR-mediated mutagenesis and inserted into pORI (forward primer: 59-GTGGTACCCTCGAGGATTGGGGACCCTG-CGCTGAACATGGAG-39 (SEQ ID NO: 5), reverse primer: 59-TCAGTCGACCTAAGCGTAATCTGGAA-CATCGTATGGGTAC-39 (SEQ ID NO: 6)). The gene encoding Core was PCR amplified from plasmid pCDNA-CORE (22) and inserted into pORI (forward primer: 59-CTGCTAGCATGGACATTGACCCTTATAAAGAAT-TTGG-39 (SEQ ID NO: 7), reverse primer: 59-CTAGGTACCACATTGAGATTCCCGAGATTGAG-39 (SEQ ID NO: 8)). The C-terminal polymerase fragment was then inserted downstream of Core using KpnI and SalI to generate fusion protein HBV core and the C terminus of polymerase (Core/PolC). The KpnI site adds a 2-amino acid (GT) linker between the two proteins. To generate 68-1 RhCMV/Core/PolC and 68-1 RhCMV/S/PolN, the pp71-encoding Rh110 gene in the 68-1 RhCMV BAC (Chang, W. L. W., et al. 2003. Cloning of the full-length rhesus cytomegalovirus genome as an infectious and self-excisable bacterial artificial chromosome for analysis of viral pathogenesis. J. Virol. 77: 5073-5083) was replaced using a modified galactokinase (galK) selection system, a two-step method that allows DNA modification without introducing unwanted heterologous sequences (Warming, S. et al. 2005. Simple and highly efficient BAC recombineering using galK selection. Nucleic Acids Res. 33: e36). It was recently demonstrated that replacement of Rh110 can be used to elicit robust Ag responses while attenuating the 68-1 RhCMV vector (Marshall, E. E., et al. 2019. Enhancing safety of cytomegalovirus-based vaccine vectors by engaging host intrinsic immunity. Sci. Transl. Med. 11: eaaw2603 10.1126/scitranslmed.aaw2603).

To delete Rh110, competent SW105 bacteria containing the 68-1 RhCMV BAC were electroporated with a PCR product containing a galK/kanamycin cassette with 50-bp flanking homology to Rh110. The bacteria were plated on kanamycin/chloramphenicol Luria Bertani agar at 30° C. for positive selection. To replace the galK/kanamycin cassette with the HBV fusion genes, a PCR product containing the HBV S-PolN fusion or HBV Core-PolC fusion with the same flanking homology to Rh110 was electroporated, and the bacteria were plated on 2-deoxy-galactose (DOG) chloramphenicol minimal media plates with glycerol as the carbon source for negative selection. PCR primers for homologous recombination were as follows: Rh110 S/PolN forward: 59-GATCACGTCATTGACACCGGCCTCCCA-CCAGCTCTCACATTCTCCGCATCACC ATGGAGAA-CATCACATCAGGAT-39 (SEQ ID NO: 9), Rh110 S/PolN reverse: 59-CAAAATATTATTACATGGTACGCAATTT-ATTGTCTATTTTCGTTATTTGTTTAT TCAAGCGTA-ATCTGGAACATCGTAT-39 (SEQ ID NO: 10) and Rh110 Core/PolC forward: 59-GATCACGTCATTGACACC-GGCCTCCCACCAGCTCTCACATTCTCCGCATCACC ATGGACATTGACCCTTATAAAGAAT-39 (SEQ ID NO: 11), Rh110 Core/PolC reverse: 59-CAAAATATTATTA-CATGGTACGCAATTTATTGTCTATTTTCGTTATTTG-TTTAT CTAAGCGTAATCTGGAACATCGTAT-39 (SEQ ID NO: 12). To generate 68-1 RhCMV/Core, we amplified the HBV core gene from pCDNA-CORE and introduced an N-terminal FLAG-tag by PCR (forward primer: 59-CTGCTAGCATGGATTACAAGGATGACAAGGA-CATCGACCCTTATAAAGAATT TGG-39 (SEQ ID NO: 13); reverse primer: 59-CTAGTCGACACATTGAGAT-TCCCGAGATTGAG-39) (SEQ ID NO: 14). The amplified product was cloned into pORI downstream of the EF1a promoter. This expression cassette was inserted into Rh211 region of 68-1 RhCMV together with a Kan resistance cassette flanked by flippase recognition target sites by homologous recombination using primers containing 50-bp homology to regions of Rh211 (forward primer: 59-GG-GAAATCACGTCATCAGGCTGGGTAGTCAACATG-GGCATACGAAACTTGCC CGAATAGATGCTCTCACT-TAACGGCTGACATG-39 (SEQ ID NO: 15), reverse primer: 59-CCAGAATGTGCTCTACTTTTTGGCCAG-CGGGGTTGGATGATTTCGCGCGTCATG GACTGCTT-CACTGTAGCTTAGTACGTTAAAC-39 (SEQ ID NO: 16)). The PCR fragment was electroporated into EL250 bacteria containing the RhCMV 68-1 BAC for in vivo recombination and recombinants selected for Kan resistance. The Kan resistance cassette was removed by temperature-inducible flippase recombination. The resulting BACs were analyzed by restriction digest, PCR analysis of recombination sites, and next-generation sequencing on an Illumina MiSeq sequencer. This sequence analysis revealed two point mutations in S/PolNthat were introduced during PCR amplification resulting in amino acid exchanges A118T and T125M in the S Ag. BAC DNA was purified using alkaline lysis, phenol/chloroform extraction, and isopropanol precipitation, and virus was reconstituted by transfection of BAC DNA using Lipofectamine 2000 (following manufacturer's protocol; Thermo Fisher Scientific) of telomerized pp71 expressing rhesus fibroblasts (Warming, S. et al. 2005. Simple and highly efficient BAC recombineering using galK selection. Nucleic Acids Res. 33: e36) or primary rhesus fibroblasts. Expression of HBV Ags was confirmed by infecting telomerized RM fibroblasts with 68-1 RhCMV/Surface/PolN or RhCMV/Core/PolC. Cells were harvested at full cytopathic effect and lysed in SDS sample buffer. 293T cells transfected (Lipofectamine 2000) with the pORI expression plasmids containing the HA-tagged HBV proteins served as positive controls. After electrophoretic separation, immunoblots were performed with anti-HA Ab MMS-101P (Covance MMS).

Two RM (RM1, RM2) were inoculated with both 68-1 RhCMV/Surface/PolN and 68-1 RhCMV/Core/PolC vectors, and two additional RM (RM3, RM4) were innoculated with a 68-1 RhCMV-based vector that expressed HBV Core under the EF1a promoter. The CD8+ T cell response against each of the Ags was longitudinally monitored by ICS, using pools of overlapping 15-mer peptides corresponding to each Ag. Longitudinal CD8+ T cell responses against these antigens in the blood of vaccinated RM were observed (FIG. 1A).

The MHC-restriction of HBV core (HBcAg)-specific CD8+ T cell responses in these animals was characterized via intracellular cytokine staining with reagents that specifically block presentation by MHC-I, MHC-II, and MHC-E as previously described (Hansen et al. 2016. Broadly targeted CD8+ T cell responses restricted by major histocompatibility complex E. Science 351: 714-720; Hansen, et al. 2013. Cytomegalovirus vectors violate CD8+ T cell epitope recognition paradigms. Science 340: 1237874-1237874.). It was found that, similar to strain 68-1 RhCMV vectors expressing SIV or *Mycobacterium tuberculosis* antigens, strain 68-1 RhCMV/HBV vector elicited HBV-specific, MHC-E- and MHC-II-restricted CD8+ T cell responses targeting a broad array of HBcAg peptides (FIG. 1).

To further confirm that the MHC-E-restriction of the RhCMV/HBV engendered the CD8+ T cell responses observed, splenocytes from a RhCMV/HBV-vaccinated RM were stimulated with K562 cells (MHC-null) transduced to express either a single human (HLA) or rhesus macaque (Mamu) MHC-E allele and pulsed with one of three individual HBcAg 15-mer peptides identified as MHC-E restricted via blocking in FIG. 1B. Only cells expressing MHC-E can present HBcAg 15-mers to these CD8+ T cells. The HBcAg-specific CD8+ T cells recognized their cognate antigen presented in the context of both HLA-E and Mamu-E (FIG. 1C). These results demonstrate the presence of MHC-E-restricted, HBV-specific CD8+ T cells in RhCMV/HBV-vaccinated RM, and further support the high functional conservation primate MHC-E molecules.

Example 2: HBV-Infected Primary Hepatocytes Express MHC-E in Vitro

Next, it was determined if primary hepatocytes express MHC-E. Primary hepatocytes (PH) were isolated from three unrelated RM and three unrelated human donors (HD). To isolate RM primary hepatocytes, a single lobe of RM liver was perfused with 200 mL pre-perfusion media (0.5 mM EGTA (Bio-World, cat #:40120128-1), 10 IU/mL heparin (Fresenius Kabi, cat #:C504730), HBSS with calcium and magnesium (Fisher Scientific, cat #:24-020-117)), followed by 200 mL HBSS without calcium and magnesium (Fisher Scientific, cat #:SH3003103) to remove remaining EGTA. Next 100 mL of collagenase media (DMEM/F12 (Gibco, cat #:11320-082), 1 mM calcium chloride (Sigma-Aldrich, cat #:C5670-100G), 20 mM HEPES (HyClone, cat #:SH30237.01) 1 mg/mL collagenase IV (Sigma-Aldrich, cat #:C9722-50MG)) warmed to 42° C. was perfused into the lobe and discarded. This was followed by re-circulation of 150 ml collagenase media through the liver lobe at 42° C. for 30 minutes to 1 hour using a rate of 75-150 mL/min, depending on the size of the liver lobe. Following collagenase perfusion, the liver was filleted with scalpels, washed over with remaining collagenase media, and media was filtered through a tea strainer. PH were washed three times in wash media (DMEM/F12, 2% bovine growth serum (HyClone, cat #:SH3054103), 23 mM HEPES buffer, 0.6 mg/ml glucose, 2 mM L-glutamine (HyClone, cat #:SH3003401), 1x antibiotic/antimycotic (HyClone, cat #:SV3007901), and 0.1 mg/mL Gentamicin (Life Technologies, cat #:15750-060)) at room temperature, with centrifugation between each wash at 50xg for 3 minutes. Prior to the third wash spin, PH were passed through a 70 μM filter to ensure single-cell suspension. PH were then suspended in 20 ml of 36% isotonic percoll (GE Healthcare, cat #:17-0891-01) in a 50 ml conical using PH media as a diluent (DMEM/F12, 10% bovine growth serum, 23 mM HEPES buffer, 0.6 mg/ml glucose, 2 mM L-glutamine, 1× antibiotic/antimycotic, and 0.1 mg/mL Gentamicin), and centrifuged at 200×g for 7 minutes. The purified PH pellet was then resuspended in room temperature PH media and counted. Collagenized plates for the hepatocytes were prepared using 0.2 mg/mL collagen R in 0.01% acetic acid (Serva, cat #:47254), left on the plate for at least 20 min prior to washing with 1 mL HBSS immediately prior to plating at $2 \times 10^5$ PH per well in a 12-well plate. Plates were placed at 37° C., 5% C02. The next day, wells were washed twice with HBSS and cultured in 1 ml PH media supplemented with 1.8% DMSO (primary hepatocyte media containing DMSO; PH-DMSO) for the remainder of the experiment.

Human donor primary hepatocytes (HD PH) were isolated from murine humanized livers and purchased from Yecuris, Inc. Humanized mice were generated with cryopreserved primary hepatocytes collected from deceased patients with the following demographics: HD1 (13 year old, female, Hispanic, HBV naïve); HD2 (13 year old, female, Caucasian, HBV naïve); HD3 (27 year old, male, Caucasian, HBV naïve).

RM and HD PH MHC presentation was determined by surface expression of bulk MHC-I via the W6/32 clone, MHC-II via HLA-DR staining, and MHC-E via the 4D12 clone. It was previously demonstrated that 4D12 specifically stains Mamu-E and not classical Mamu-Ia molecules. All three human donors shared one HLA-A and one HLA-C allele (Table 1). Thus, before proceeding it was confirmed that the MHC-E-specific 4D12 clone stains only HLA-E and not the HLA-A or -C molecules shared between the three HD (FIG. 2A). Expression of MHC-E was examined by staining and majority of primary hepatocytes from both species expressed MHC-E (FIGS. 2B and 2C).

TABLE 1

| | | | MHC Genotypes of HD PH | | | |
|---|---|---|---|---|---|---|
| | HLA-A | HLA-A | HLA-B | HLA-B | HLA-C | HLA-C |
| HD1 | 02:17 | 02:01 | 40:02 | 50:01 | 03:05 | 06:02 |
| HD2 | 01:01 | 02:01 | 15:XX* | 37:XX* | 03:03 | 06:02 |
| HD3 | 02:01 | 02:01 | 57:01 | 27:05 | 02:02 | 06:02 |

XX* denotes an undetermined allele.

To determine if HBV infection influences the expression of MHC-E on the surface of primary hepatocytes, primary hepatocytes were collected from the same HBV infected human donor. One day after plating isolated rhesus macaque primary hepatocytes, replication-incompetent adenovirus serotype 5 expressing human NTCP (MOI 10) under the liver-specific TTR promoter was added to the culture for 2 days. On the second day, cells were re-fed with 1 ml PH-DMSO media. On the fourth day following adenovirus transduction, primary hepatocytes were washed twice in 1 ml HBSS and overlaid with HBV-containing media at an MOI of 100 (PH-DMSO containing 4% PEG6000, Sigma-Aldrich, cat #:81253-250G) and incubated overnight. The next morning, wells were washed three times with 1 ml HBSS and then cultured in 1 ml primary hepatocytes-DMSO for the remainder of the experiment.

One day after plating, human donor primary hepatocytes were overlaid with HBV-containing media at an MOI of 100 (PH-DMSO containing 4% PEG6000, Sigma-Aldrich, cat #:81253-250G) and incubated overnight. The next morning, wells were washed three times with 1 ml HBSS and then cultured in 1 ml primary hepatocytes-DMSO for the remainder of the experiment.

HBV infection of human donor primary hepatocytes was confirmed by measuring the level of HBV envelope antigen (HBeAg) in the supernatant prior to staining of the cells. Primary hepatocytes were co-stained with MHC markers (MHC-I, MHC-E, and MHC-II) along with intracellular HBcAg on day 4 post-HBV infection, since this was the first time point where intracellular HBcAg was detectable. Strong staining with the 4D12 antibody was observed on both HBV-infected and HBV-naïve PH, indicating high levels of MHC-E expression (FIGS. 2D and 2E). In contrast, HLA-DR expression was minimal or absent in all three human donor primary hepatocytes samples, in line with previously published results (Senaldi et al. 1991. Class I and class II major histocompatibility complex antigens on hepatocytes: importance of the method of detection and expression in histologically normal and diseased livers. J. Clin. Pathol. 44: 107-114.). It is possible that ex vivo manipulation of the primary hepatocytes prior to assessing surface MHC levels induced a fraction of these cells to lose MHC-E expression. Nevertheless, taken together, these results showed that HBV-infected primary hepatocytes express MHC-E and that MHC-E could represent a potential HBV-specific CD8+ T cell restriction element.

Example 3: MHC-E-Restricted CD8+ T Cells from
RHCMV/HBV-Inoculated Rhesus Macaques
Recognize HBV-Infected Allogenic and Xenogenic
Primary Hepatocytes The MHC study revealed high levels of MHC-E expression on human donor and rhesus macaque primary hepatocytes, regardless of HBV infection. It was therefore hypothesized that CD8+ T cells from RhCMV/HBV inoculated rhesus macaques would recognize allogeneic, HBV-infected rhesus macaque primary hepatocytes given the high functional conservation of MHC-E in primates. In support of this hypothesis, CD8+ T cells (bulk splenocytes and purified CD8β+ T cells) from RM1 and RM2 recognized HBV-infected primary hepatocytes from two unrelated rhesus macaque donors, but did not respond to HBV-naïve primary hepatocytes (FIG. 3A).

In order to more comprehensively determine the MHC-restriction of CD8+ T cells recognizing HBV-infected primary hepatocytes targets, a series of recognition experiments were performed using MHC-specific blocking reagents shown in FIG. 1.

Prior to HBV infection, one well of primary hepatocytes was collected and stained as a baseline. Starting on day two post-infection, a well each of HBV-infected and HBV-naïve primary hepatocytes was collected with 0.5% trypsin-EDTA (Fisher Scientific, cat #: SH30236.01) and washed twice in ice cold FACS buffer (PBS, Fisher Scientific, cat #:SH30256FS, with 10% fetal bovine serum). Cells were incubated with anti-HLA-E antibody (clone: 4D12, Origene, cat #: LS-C179742) for 30 minutes at 4° C., washed twice in ice cold FACS buffer, and incubated with F(ab)2-Goat anti-mouse IgG (H L)-APC (Invitrogen, cat #: A10539) for 30 minutes at 4° C. Cells were then washed twice in ice cold PBS and incubated with pan-MHC-I-PerCP-Cy5.5 (clone: W6/32, Biolegend Inc., cat #: 311419), anti-HLA-DR Alexa 700 (clone: L243 (BD Biosciences, cat #: 560743), and Live/Dead fixable yellow (Invitrogen, cat #: L-34959) for 30 minutes at 4° C. Cells were washed in FACS buffer and fixed using Foxp3/Transcription Factor Staining Buffer Set (eBioscience, cat #: 00-5523-00) for one hour at room temperature. Prior to fixation all wash spins were performed at 350×g for 3 minutes. After fixation, cells were suspended in permeabilization buffer (eBioscience, cat #: 00-8333-56). All wash spins after fixation were performed at 830×g for 3 minutes. Primary hepatocytes were incubated for one hour at 4° C. with Hepatitis B Virus Core Antigen Antibody (clone: 13A9, Fisher Scientific, cat #: MA1-7606) conjugated to R-phycoerythrin (PE) using the Lightning-Link R-PE kit (Innova Biosciences, cat #: 703-0005). Cells were washed three times in permeabilization buffer and then collected on a Becton-Dickenson LSR-II. Analysis was performed on FlowJo X (TreeStar Inc.). In all analyses, gating on the light scatter signature of large, complex PH was followed by assessment of specific MHC and HBV markers.

HBV-specific CD8+ T cell responses were measured in mononuclear cell preparations from the spleens of RhCMV/HBV vaccinated RM by flow cytometric ICS. Briefly, splenocytes or isolated CD8β+ T cells were incubated with HBV-infected or HBV naïve primary hepatocytes targets and the co-stimulatory molecules CD28 and CD49d (BD Biosciences) for 1 hour, followed by addition of brefeldin A (Sigma-Aldrich) for an additional 8 hours. Co-stimulation without primary hepatocytes target co-culture served as a background control. The MHC-restriction of a response was determined by pre-incubating PH targets for 1 hour at room temperature in the presence of pan anti-MHC-I antibody (25

μg/ml; clone: W6-32), VL9 peptide (20 uM), CLIP peptide (MHC-II-associated in-variant chain, amino acids 89 to 100; 10 μg/ml), or anti-HLA-DR antibody (10 μg/ml; clone: L243) before co-culturing with target primary hepatocytes cells. Stimulated cells were fixed, permeabilized, and stained, and flow cytometric analysis was performed on an LSR-II instrument (BD Biosciences). Analysis was done using FlowJo X software (Tree Star, Inc.). In all analyses, gating on the light scatter signature of small lymphocytes was followed by progressive gating on the CD3+ population and then the CD4−/CD8+ T cell subset. Antigen-specific response frequencies for CD8+ T cell populations were routinely determined by intracellular expression of IFN-γ.

HBV-infected or HBV-naïve targets were collected at day 6 post-HBV infection (MOI=100), incubated with the blocking agents W6/32 antibody (pan MHC-I), VL9 peptide (MHC-E), CLIP (MHC-II), or HLA-DR antibody (MHC-II), and then co-cultured with splenocytes or isolated CD8β+ T cells overnight. Following co-culture, CD8+ T cells were stained intracellularly for IFN-γ and TNF-α to assess recognition of the targets. CD8+ T cell recognition of HBV-infected RM PH was blocked with W6/32 antibody and VL9 peptide, but not with CLIP or HLA-DR, indicating that the entirety of the response to HBV-infected targets was MHC-E restricted (FIG. 3A).

Because MHC-E is functionally conserved across primates, it was hypothesized that CD8+ T cells from RhCMV/HBV inoculated RM would also recognize HBV-infected HD primary hepatocytes. To test this hypothesis, similar recognition experiments were performed by incubating splenocytes and purified CD8+ T cells from the same RhCMV/HBV inoculated macaques (RM1 and RM2) with HBV-infected human donor primary hepatocytes. As hypothesized, these CD8+ T cells recognized HBV-infected, xenogeneic human donor primary hepatocytes (FIG. 3B). As described above for the rhesus macaque primary hepatocytes target co-culture experiments, the CD8+ T cell recognition of HBV-infected human donor primary hepatocytes was completely blocked by the MHC-E-binding VL9 peptide. Taken together, these results definitively show that HBV-infected primary hepatocytes present HBV antigen in the context MHC-E, indicating that this pathway can be exploited to target CD8+ T cells to HBV-infected cells.

Next, the conservation of two 15-mer peptides, Core 7 (PSVRDLLDTASALYR; SEQ ID NO: 17) and Core 14 (TALRQAILCWGELMT; SEQ ID NO: 18) MHC-E-bound supertope in the HBV core antigen was examined. 6,203 full genome HBV sequences spanning all known HBV genotypes were retrieved from The Hepatitis B Virus Database, translated, and amino acid sequences aligned against Core 7 (FIG. 4A) and Core 14 (FIG. 4B). There was high conservation within the two 15-mer peptides that generated MHC-E-restricted CD8+ T cell responses in all animals assayed (supertopes). Importantly, in the two positions not highly conserved (position 3 Core 7 and position 15 Core 14), there is only one additional dominant amino acid globally amongst HBV strains at this position. Thus, over 98% of known global sequences express one of two amino acids at these positions.

These results identify a completely new set of CD8+ T cell responses against HBV, which paves the way for development of innovative HBV therapeutics. While MHC-E-restricted CD8+ T cell responses have been identified in natural viral infections with CMV, EBV, and HCV (Joosten et al. 2016. Characteristics of HLA-E Restricted T-Cell Responses and Their Role in Infectious Diseases. Journal of Immunology Research 2016: 1-11), no reports of MHC-E- restricted CD8+ T cells responses against HBV have been published. Therefore, it was unclear whether HBV-infected hepatocytes presented HBV antigens in the context of MHC-E. These results show that MHC-E does present HBV antigens on the surface of HBV-infected cells and that CD8+ T cells from a completely distinct primate species can recognize these MHC-E:peptide complexes.

Outside of representing a completely unique type of CD8+ T cells response against HBV, the breadth of epitopes targeted within HBcAg indicates that therapeutic vaccination with CMV/HBV vectors would elicit broadly-targeted CD8+ T cell responses. While this broad targeting has been shown previously against SIV, *Mycobacterium tuberculosis*, and malaria, it may be particularly efficacious against HBV, since the vast majority of the HBV genome is comprised almost exclusively of non-plastic overlapping reading frames. Together, these results show for the first time that MHC-E-restricted CD8+ T cells can be harnessed for the treatment of chronic HBV infection, either through therapeutic vaccination or adoptive immunotherapy.

---

What is claimed is:

1. A method of generating an immune response to a hepatitis B virus (HBV) in a subject, the method comprising administering to the subject a cytomegalovirus (CMV) vector expressing a HBV antigen in an amount effective to elicit a CD8+ T cell response to the HBV antigen, wherein the CMV vector does not express UL128, UL130, UL146, and UL147 proteins or orthologs thereof, wherein the hepatitis B antigen is PSVRDLLDTASALYR (SEQ ID NO: 17) or TALRQAILCWGELMT (SEQ ID NO: 18).

2. The method of claim 1, wherein the hepatitis B antigen is PSVRDLLDTASALYR (SEQ ID NO: 17).

3. The method of claim 1, wherein the hepatitis B antigen is TALRQAILCWGELMT (SEQ ID NO: 18).

4. The method of claim 1, wherein at least 10% of the CD8+ T cells elicited by the CMV vector are restricted by MHC-E or an ortholog thereof, or MHC-II or an ortholog thereof.

5. The method of claim 1, wherein fewer than 10% of the CD8+ T cells elicited by the CMV vector are restricted by MHC-class 1$a$ or an ortholog thereof.

6. The method of claim 4, wherein some of the CD8+ T cells restricted by MHC-E recognize epitopes shared by at least 90% of other subjects immunized with the vector.

* * * * *